United States Patent [19]

Müller et al.

[11] Patent Number: 5,786,361
[45] Date of Patent: Jul. 28, 1998

[54] PYRIDAZINO-, PYRIMIDO-, PYRAZINO- AND TRIAZINOINDOLES, -PYRROLOCYCLOALKENES OR PYRROLOOXOCYCLOALKENES, OR PYRIDOPYRROLYLPYRIDO COMPOUNDS, COMPOSITIONS CONTAINING THEM, AND USE THEREOF TO TREAT ATHEROSCLEROSIS

[75] Inventors: Ulrich Müller, Wuppertal; Peter Eckenberg, Erkrath; Rudi Grützmann, Solingen; Hilmar Bischoff, Wuppertal; Dirk Denzer, Wuppertal; Ulrich Nielsch, Wuppertal, all of Germany

[73] Assignee: Bayer Aktiengesellschaft, Leverkusen, Germany

[21] Appl. No.: 837,076

[22] Filed: Apr. 11, 1997

[30] Foreign Application Priority Data

Apr. 11, 1997 [DE] Germany .................. 196 15 265.8

[51] Int. Cl.⁶ ............... A61K 31/505; A61K 31/44; A61K 31/495; A61K 31/53; C07D 487/04; C07D 471/04; C07D 487/14

[52] U.S. Cl. ............... 514/267; 514/243; 514/248; 514/250; 514/257; 514/292; 514/293; 544/183; 544/184; 544/233; 544/234; 544/246; 544/247; 544/250; 544/251; 544/343; 544/345; 546/82; 546/85

[58] Field of Search ............... 514/243, 248, 514/250, 257, 267, 292, 293; 544/183, 184, 233, 234, 246, 247, 250, 343, 345, 251; 546/82, 85

[56] References Cited

U.S. PATENT DOCUMENTS 5,238,248 8/1993 Hubschwerlen et al. .......... 544/250
5,306,820 4/1994 Decker et al. .................. 546/153

5,585,490 12/1996 Thurkauf et al. .................. 544/250

FOREIGN PATENT DOCUMENTS 0313480 12/1989 Japan.
6220059 8/1994 Japan.

OTHER PUBLICATIONS

J. Clark und I. W. Souton, J. Chem. Soc. Perkin Trans. I, 1814 (1974).
T.D. Duffy und D.G. Wibberley, J. Chem. Soc., Perkin Trans. I, 1921 (1974).
Y. Kondo, R. Watanabe, T. Sakamoto und H. Yamanaka, Chem. Pharm. Bull., 37, 2933 (1989).
S. Senda, K. Hirota und G.N. Yang, Chem. Pharm. Bull. 20, 399 (1982).
S. Senda, K. Hirota und M. Takahashi, J. Chem. Soc., Perkin Trans. I, 503 (1975).

*Primary Examiner*—Yogendra N. Gupta
*Attorney, Agent, or Firm*—Sprung Kramer Schaefer & Briscoe

[57] ABSTRACT

Compounds of the formula (I):

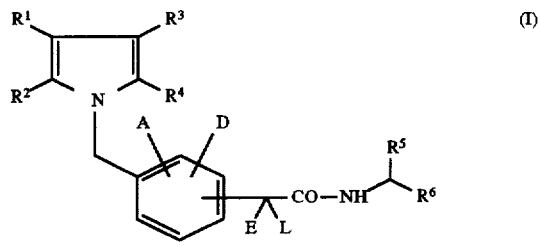

are prepared by reaction of the phenylacetic acid derivatives substituted by the appropriate heterocycles, optionally in an activated form, with phenylglycinols. The compounds are suitable as active compounds in medicaments, in particular in medicaments having antiatherosclerotic activity.

7 Claims, No Drawings

PYRIDAZINO-, PYRIMIDO-, PYRAZINO- AND TRIAZINOINDOLES, -PYRROLOCYCLOALKENES OR PYRROLOOXOCYCLOALKENES, OR PYRIDOPYRROLYLPYRIDO COMPOUNDS, COMPOSITIONS CONTAINING THEM, AND USE THEREOF TO TREAT ATHEROSCLEROSIS

The present invention relates to new pyridazino-, pyrimido-, pyrazino- and triazino-indoles, processes for their preparation and their use as medicaments, in particular as antiatherosclerotic medicaments.

It is known that raised blood levels of triglycerides (hypertriglyceridaemia) and cholesterol (hypercholesterolaemia) are associated with the genesis of atherosclerotic vascular wall changes and coronary heart diseases.

A distinctly increased risk of the development of coronary heart disorders moreover exists if these two risk factors occur in combination, which is in turn accompanied by an overproduction of apoliprotein B-100. There is therefore still a great need to make available effective medicaments for the control of atherosclerosis and of coronary heart diseases.

The present invention relates to pyridazino-, pyrimido-, pyrazino- and triazino-indoles of the general formula (I)

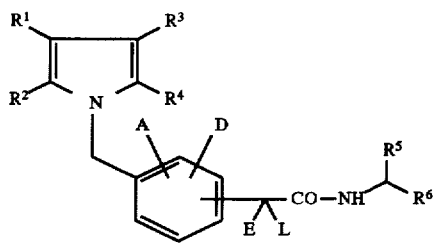

in which $R^1$ and $R^2$, including the double bond connecting them, together form a phenyl ring or a 5- to 8-membered cycloalkene or oxocycloalkene ring, which is optionally substituted up to 3 times in an identical or different manner by halogen, trifluoromethyl, carboxyl, hydroxyl, by straight-chain or branched alkoxy or alkoxycarbonyl each having up to 6 carbon atoms or by straight-chain or branched alkyl having up to 6 carbon atoms, which for its part can be substituted by hydroxyl or by straight-chain or branched alkoxy having up to 4 carbon atoms, $R^3$ and $R^4$, including the double bond, together form a radical of the formula

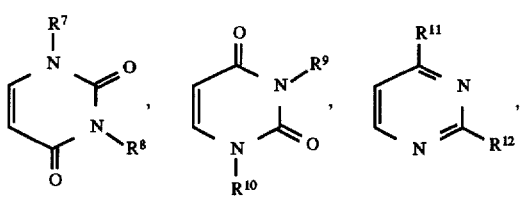

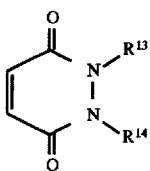

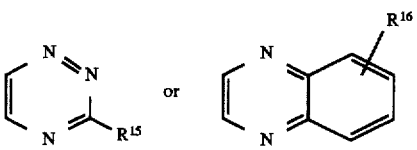

in which $R^7$, $R^8$, $R^9$, $R^{10}$, $R^{11}$, $R^{12}$, $R^{13}$, $R^{14}$, $R^{15}$ and $R^{16}$ are identical or different and denote hydrogen, carboxyl, straight-chain or branched alkoxy, alkylthio, acyl or alkoxycarbonyl each having up to 6 carbon atoms or straight-chain or branched alkyl having up to 6 carbon atoms, which is optionally substituted by hydroxyl, or $R^1$ and $R^2$, including the double bond, form a pyridyl ring, and $R^3$ and $R^4$, likewise including the double bond, together form a pyridyl ring, both pyridyl rings optionally being substituted up to 3 times in an identical or different manner by halogen, trifluoromethyl, carboxyl, hydroxyl, by straight-chain or branched alkoxy or alkoxycarbonyl each having up to 6 carbon atoms or by straight-chain or branched alkyl having up to 6 carbon atoms, which for its part is substituted by hydroxyl or by straight-chain or branched alkoxy having up to 4 carbon atoms, A and D are identical or different and represent hydrogen, halogen, trifluoromethyl, hydroxyl or straight-chain or branched alkyl or alkoxy each having up to 5 carbon atoms, E and L are identical or different and represent hydrogen, cycloalkyl having 3 to 8 carbon atoms or straight-chain or branched alkyl having up to 10 carbon atoms, which is optionally substituted by cycloalkyl having 3 to 6 carbon atoms, or represent phenyl which is optionally substituted by halogen or trifluoromethyl, or E and L, together with the carbon atom, form a 4-8-membered cycloalkyl ring, $R^5$ represents phenyl or a 5- to 7-membered saturated or unsaturated heterocycle having up to 3 heteroatoms from the series S, N and/or O, the cycles optionally being substituted up to 3 times in an identical or different manner by nitro, carboxyl, halogen, cyano or by straight-chain or branched alkenyl or alkoxycarbonyl each having up to 6 carbon atoms or by straight-chain or branched alkyl having up to 6 carbon atoms, which is optionally substituted by hydroxyl, carboxyl or by straight-chain or branched alkoxy or alkoxycarbonyl each having up to 6 carbon atoms, and/or the cycles optionally being substituted by a group of the formula —$OR^{17}$ or —$NR^{18}R^{19}$, in which $R^{17}$ denotes hydrogen or straight-chain or branched alkyl or alkenyl each having up to 6 carbon atoms, $R^{18}$ and $R^{19}$ are identical or different and denote phenyl, hydrogen or straight-chain or branched alkyl having up to 6 carbon atoms or denote straight-chain or branched acyl having up to 8 carbon atoms, which is optionally substituted by a group of the formula —NR$^{20}$R$^{21}$, in which R$^{20}$ and R$^{21}$ are identical or different and denote hydrogen or straight-chain or branched acyl having up to 8 carbon atoms, R$^6$ represents hydrogen, carboxyl or straight-chain or branched alkoxycarbonyl having up to 5 carbon atoms, or represents straight-chain or branched alkyl having up to 6 carbon atoms, which is optionally substituted by hydroxyl or by a group of the formula —O—CO—R$^{22}$, in which R$^{22}$ denotes phenyl which is optionally substituted up to 3 times in an identical or different manner by halogen, hydroxyl or by straight-chain or branched alkyl having up to 5 carbon atoms, or denotes straight-chain or branched alkyl or alkenyl each having up to 22 carbon atoms, each of which is optionally substituted by a group of the formula —OR$^{23}$, in which R$^{23}$ denotes hydrogen, benzyl, triphenylmethyl or straight-chain or branched acyl having up to 6 carbon atoms, if appropriate in an isomeric form, and their salts.

The pyridazino-, pyrimido-, pyrazino- and triazinoindoles according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Those particularly preferred are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

The cycloalkene radical (R$^1$/R$^2$), including the double bond of the parent structure, in the context of the invention in general represents a 5- to 8-membered, preferably 5- to 7-membered, hydrocarbon radical such as, for example, a cyclobutene, cyclopentene, cyclohexene or cycloheptene radical. The cyclopentene, cyclohexene, cyclooctene and cycloheptene radicals are preferred.

Heterocycle in the context of the invention in general represents a saturated or unsaturated 5- to 7-membered, preferably 5- to 6-membered, heterocycle which can contain up to 3 heteroatoms from the series S, N and/or O. Examples which may be mentioned are: pyridyl, thienyl, furyl, pyrrolyl, thiazolyl, oxazolyl, imidazolyl, morpholinyl or piperidyl. Pyridyl and thienyl are preferred.

The compounds according to the invention can exist in stereoisomeric forms which either behave as image and mirror image (enantiomers), or which do not behave as image and mirror image (diastereomers). The invention relates both to the enantiomers and diastereomers or their respective mixtures. These mixtures of the enantiomers and diastereomers can be separated into the stereoisomerically uniform constituents in a known manner.

Preferred compounds of the general formula (I) are those in which

R$^1$ and R$^2$, including the double bond connecting them, together form a phenyl ring or a cyclopentene, cyclohexene, cycloheptene, cyclooctene, oxocyclopentene, oxocyclohexene, oxocycloheptene or oxocyclooctene radical, which is optionally substituted up to 2 times in an identical or different manner by fluorine, chlorine, bromine, trifluoromethyl, carboxyl, hydroxyl, by straight-chain or branched alkoxy or alkoxycarbonyl each having up to 4 carbon atoms or by straight-chain or branched alkyl having up to 4 carbon atoms, which for its part can be substituted by hydroxyl or by straight-chain or branched alkoxy having up to 3 carbon atoms, R$^3$ and R$^4$, including the double bond, together form a radical of the formula

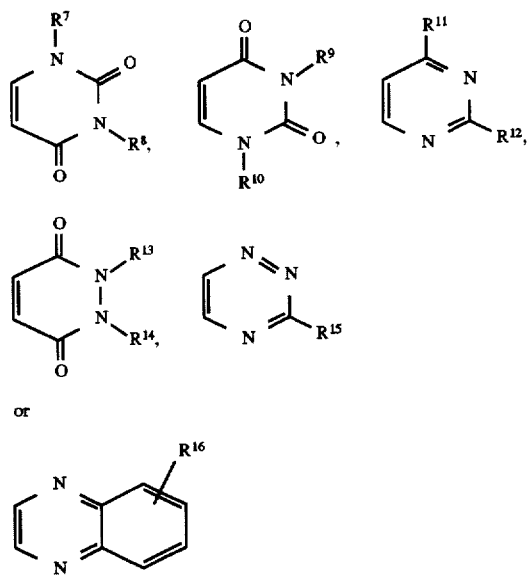

in which

R$^7$, R$^8$, R$^9$, R$^{10}$, R$^{11}$, R$^{12}$, R$^{13}$, R$^{14}$, R$^{15}$ and R$^{16}$ are identical or different and denote hydrogen, straight-chain or branched alkoxy, alkylthio, acyl or alkoxycarbonyl each having up to 4 carbon atoms or straight-chain or branched alkyl having up to 4 carbon atoms, which is optionally substituted by hydroxyl, or R$^1$ and R$^2$, including the double bond, form a pyridyl ring, and R$^3$ and R$^4$, likewise including the double bond, together form a pyridyl ring, both pyridyl rings optionally being substituted up to 2 times in an identical or different manner by fluorine, chlorine, bromine, trifluoromethyl, carboxyl, hydroxyl, by straight-chain or branched alkoxy or alkoxycarbonyl each having up to 4 carbon atoms or by straight-chain or branched alkyl having up to 4 carbon atoms, which for its part is substituted by hydroxyl or by straight-chain or branched alkoxy having up to 3 carbon atoms, A and D are identical or different and represent hydrogen, fluorine, chlorine, bromine, trifluoromethyl, hydroxyl or straight-chain or branched alkyl or alkoxy each having up to 4 carbon atoms, E and L are identical or different and represent hydrogen, cyclopropyl, cyclobutyl, cyclopentyl, cyclohexyl, cycloheptyl, cyclooctyl or straight-chain or branched alkyl having up to 8 carbon atoms, which is optionally substituted by cyclopropyl, cyclopentyl or cyclohexyl, or represent phenyl which is optionally substituted by fluorine, chlorine or bromine, or E and L, together with the carbon atom, form a 4-7-membered cycloalkyl ring, $R^5$ represents phenyl, pyridyl, furyl, thienyl or imidazolyl, each of which is optionally substituted up to 2 times in an identical or different manner by nitro, carboxyl, fluorine, chlorine, bromine, cyano, by straight-chain or branched alkenyl or alkoxycarbonyl each having up to 4 carbon atoms or by straight-chain or branched alkyl having up to 5 carbon atoms, which is optionally substituted by hydroxyl, carboxyl or by straight-chain or branched alkoxy or alkoxycarbonyl each having up to 5 carbon atoms, and/or the cycles are optionally substituted by a group of the formula —$OR^{17}$ or —$NR^{18}R^{19}$, in which $R^{17}$ denotes hydrogen or straight-chain or branched alkyl or alkenyl each having up to 4 carbon atoms, $R^{18}$ and $R^{19}$ are identical or different and denote phenyl, hydrogen or straight-chain or branched alkyl having up to 5 carbon atoms, or denote straight-chain or branched acyl having up to 6 carbon atoms, which is optionally substituted by a group of the formula —$NR^{20}R^{21}$, in which $R^{20}$ and $R^{21}$ are identical or different and denote hydrogen or straight-chain or branched acyl having up to 6 carbon atoms, $R^6$ represents hydrogen, carboxyl or straight-chain or branched alkoxycarbonyl having up to 4 carbon atoms, or represents straight-chain or branched alkyl having up to 5 carbon atoms, which is optionally substituted by hydroxyl or by a group of the formula —O—CO—$R^{22}$, in which $R^{22}$ denotes phenyl which is optionally substituted up to 3 times in an identical or different marmer by fluorine, chlorine, bromine, hydroxyl or by straight-chain or branched alkyl having up to 4 carbon atoms, or denotes straight-chain or branched alkyl or alkenyl each having up to 20 carbon atoms, each of which is optionally substituted by a group of the formula —$OR^{23}$, in which $R^{23}$ denotes hydrogen, benzyl, triphenylmethyl or straight-chain or branched acyl having up to 5 carbon atoms, if appropriate in an isomeric form, and their salts.

Particularly preferred compounds of the general formula (I) are those in which $R^1$ and $R^2$, including the double bond connecting them, together form a phenyl ring or a cyclopentene, cyclohexene, cycloheptene, cyclooctene, oxocyclopentene, oxocyclohexene, oxocycloheptene or oxocyclooctene radical, which is optionally substituted up to 2 times in an identical or different manner by fluorine, chlorine, bromine, trifluoromethyl, carboxyl, hydroxyl, by straight-chain or branched alkoxy or alkoxycarbonyl each having up to 3 carbon atoms or by straight-chain or branched alkyl having up to 3 carbon atoms, which for its part can be substituted by hydroxyl, methoxy or ethoxy, $R^3$ and $R^4$, including the double bond, together form a radical of the formula

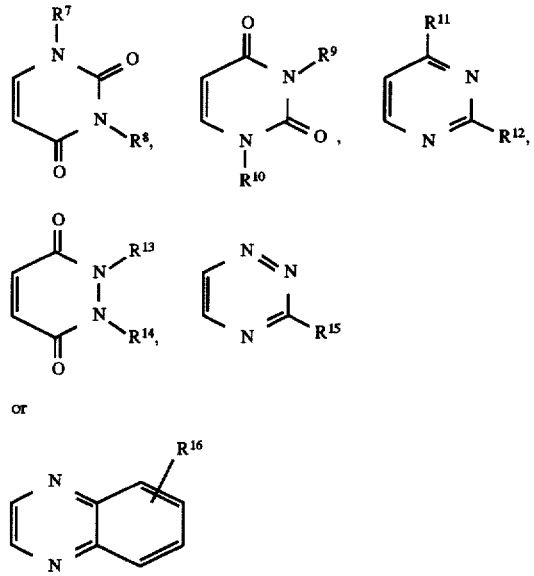

in which $R^7$, $R^8$, $R^9$, $R^{10}$, $R^{11}$, $R^{12}$, $R^{13}$, $R^{14}$, $R^{15}$ and $R^{16}$ are identical or different and denote hydrogen, straight-chain or branched alkoxy or alkylthio each having up to 3 carbon atoms or straight-chain or branched alkyl having up to 3 carbon atoms, which is optionally substituted by hydroxyl, or $R^1$ and $R^2$, including the double bond, form a pyridyl ring, and $R^3$ and $R^4$, likewise including the double bond, together form a pyridyl ring, both pyridyl rings optionally being substituted up to 2 times in an identical or different manner by fluorine, chlorine, bromine, trifluoromethyl, carboxyl, hydroxyl, by straight-chain or branched alkoxy or alkoxycarbonyl each having up to 3 carbon atoms or by straight-chain or branched alkyl having up to 3 carbon atoms, which for its part is substituted by hydroxyl, methoxy or ethoxy, A and D are identical or different and represent hydrogen, fluorine, chlorine, bromine or trifluoromethyl, E and L are identical or different and represent hydrogen, cyclopropyl, cyclobutyl, cyclopentyl, cyclohexyl, cycloheptyl, cyclooctyl or straight-chain or branched alkyl having up to 6 carbon atoms, which is optionally substituted by cyclopentyl or cyclohexyl, or represent phenyl which is optionally substituted by fluorine, chlorine or bromine, or E and L, together with the carbon atom, form a 5-7-membered cycloalkyl ring, $R^5$ represents phenyl, pyridyl or thienyl, each of which is optionally substituted up to 2 times in an identical or different manner by nitro, carboxyl, fluorine, chlorine, bromine, cyano, by straight-chain or branched alkenyl or alkoxycarbonyl each having up to 3 carbon atoms or by straight-chain or branched alkyl having up to 4 carbon atoms, which is optionally substituted by hydroxyl, carboxyl or by straight-chain or branched alkoxy or alkoxycarbonyl each having up to 4 carbon atoms, and/or the cycles are optionally substituted by a group of the formula —OR$^{17}$ or —NR$^{18}$R$^{19}$, in which R$^{17}$ denotes hydrogen or straight-chain or branched alkyl or alkenyl each having up to 3 carbon atoms, R$^{18}$ and R$^{19}$ are identical or different and denote phenyl, hydrogen or straight-chain or branched alkyl having up to 4 carbon atoms, or denote straight-chain or branched acyl having up to 5 carbon atoms, which is optionally substituted by a group of the formula —NR$^{20}$R$^{21}$, in which R$^{19}$ and R$^{20}$ are identical or different and denote hydrogen or straight-chain or branched acyl having up to 5 carbon atoms, R$^6$ represents hydrogen, carboxyl or straight-chain or branched alkoxycarbonyl having up to 3 carbon atoms, or represents straight-chain or branched alkyl having up to 4 carbon atoms, which is optionally substituted by hydroxyl or by a group of the formula —O—CO—R$^{22}$, in which R$^{22}$ denotes phenyl which is optionally substituted up to 3 times in an identical or different manner by straight-chain or branched alkyl having up to 3 carbon atoms, or denotes straight-chain or branched alkyl or alkenyl each having up to 19 carbon atoms, each of which is optionally substituted by a group of the formula —OR$^{23}$, in which R$^{23}$ denotes hydrogen, benzyl, triphenylmethyl or straight-chain or branched acyl having up to 4 carbon atoms, if appropriate in an isomeric form, and their salts.

Very particularly preferred compounds of the general formula (I) are those in which A and D represent hydrogen.

A process for the preparation of the compounds of the general formula (I) according to the invention has additionally been found, characterized in that racemic or alternatively already enantiomerically pure carboxylic acids or their activated derivatives of the general formula (II)

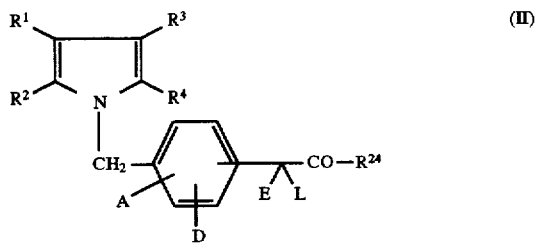

in which

A, D, E, L, R$^1$, R$^2$, R$^3$ and R$^4$ have the meaning indicated above, and

R$^{24}$ represents hydroxyl or an activating radical, preferably chloride, are amidated with compounds of the general formula (III)

in which

R$^5$ and R$^6$ have the meaning indicated above, in inert solvents, if appropriate in the presence of bases and/or auxiliaries.

The process according to the invention can be illustrated by way of example by the following equation:

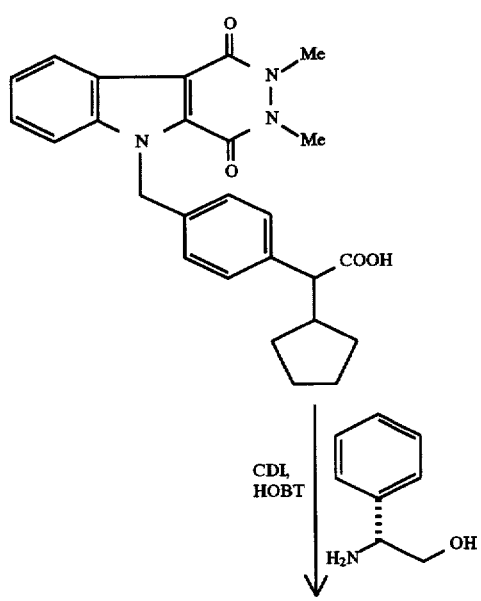

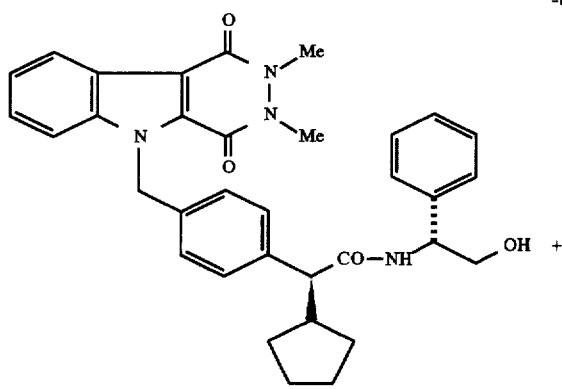 + 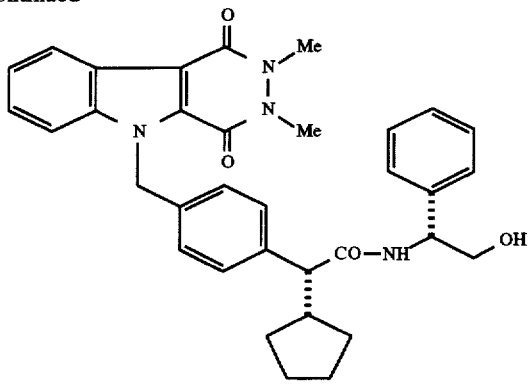

Suitable solvents here for the amidation are inert organic solvents which do not change under the reaction conditions. These include ethers, such as diethyl ether or tetrahydrofuran, halogenohydrocarbons such as dichloromethane, trichloromethane, tetrachloromethane, 1,2-dichloroethane, trichloroethane, tetrachloroethane, 1,2-dichloroethylene or trichloroethylene, hydrocarbons such as benzene, xylene, toluene, hexane, cyclohexane, or petroleum fractions, nitromethane, dimethylformamide, acetone, acetonitrile or hexamethylphosphoramide. It is also possible to employ mixtures of the solvents. Dichloromethane, tetrahydrofuran, acetone and dimethylformamide are particularly preferred.

Bases which can be employed for the process according to the invention are in general inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, or alkali metal or alkaline earth metal alkoxides such as sodium or potassium methoxide, sodium or potassium ethoxide or potassium tert-butoxide, or organic amines (trialkyl($C_1$–$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ as bases alkali metals such as sodium and their hydrides such as sodium hydride. Sodium and potassium carbonate and triethylamine are preferred.

The base is employed in an amount from 1 mol to 5 mol, preferably from 1 mol to 3 mol, relative to 1 mol of the compound of the general formula (II).

The reaction is in general carried out in a temperature range from 0° C. to 150° C., preferably from +20° C. to +110° C.

The reaction can be carried out at normal, elevated or reduced pressure (e.g. 0.5 to 5 bar). In general, the reaction is carried out at normal pressure.

The reaction can optionally also proceed via the activated stage of the acid halides, which can be prepared from the corresponding acids by reaction with thionyl chloride, phosphorus trichloride, phosphorus pentachloride, phosphorus tribromide or oxalyl chloride.

The abovementioned bases can also be employed as acid-binding auxiliaries for the amidation.

Suitable auxiliaries are also dehydrating reagents. These include, for example, carbodiimides such as diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphonic anhydride or isobutyl chloroformate or benzotriazolyloxy-tris-(dimethylamino)phosphonium hexa-fluorophosphate or diphenyl phosphoramidate or methane-sulphonyl chloride, if appropriate in the presence of bases such as triethylamine or N-ethylmorpholine or N-methylpiperidine or dicyclohexylcarbodiimide and N-hydroxysuccinimide.

The auxiliaries are in general employed in an amount from 0.5 to 3 mol, preferably from 1 to 1.5 mol, relative to 1 mol of the appropriate carboxylic acids.

The carboxylic acids of the general formula (II) can be prepared by first preparing, by reaction of compounds of the general formula (IV)

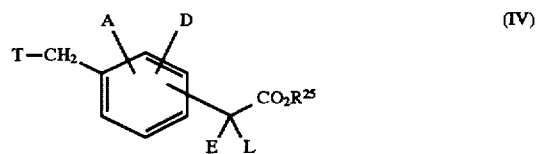

(IV)

in which

A, D, E and L have the meaning indicated above,

T represents a typical leaving group such as, for example, chlorine, bromine, iodine, tosylate or mesylate, preferably bromine, and $R^{25}$ represents ($C_1$–$C_4$)-alkyl, with compounds of the general formula (V)

(V)

in which $R^1$, $R^2$, $R^3$ and $R^4$ have the meaning indicated above, the compounds of the general formula (VI)

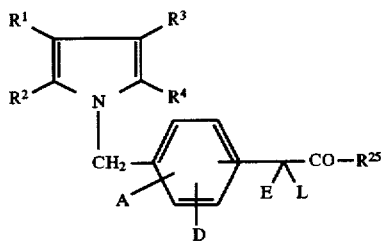

(VI)

in which

A, D, E, L, $R^1$, $R^2$, $R^3$, $R^4$ and $R^{25}$ have the meaning indicated above, in inert solvents, if appropriate in the presence of a base, and then hydrolysing the esters according to customary methods.

The enantiomerically pure acids, i.e. compounds of the formula (II) in which E and L must be different, are moreover obtained by, starting from the D- or L-menthyl esters of the general formula (VII)

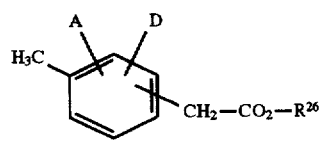

(VII)

in which

A and D have the meaning indicated above and $R^{26}$ represents D- or L-menthyl, by reaction with compounds of the general formulae (VIIIa) and (VIIIb)

E—Z (VIIIa)

L—Z (VIIIb)

in which

E and L are different and otherwise have the meaning indicated, and

Z represents halogen, preferably bromine, preparing the enantiomerically pure menthyl esters of the general formulae (IXa) and (IXb)

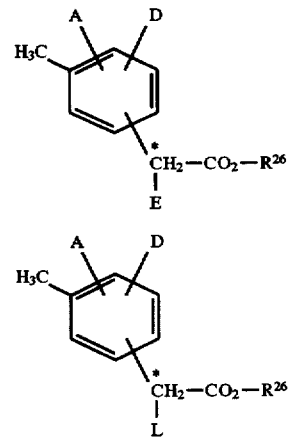

(IXa)

(IXb)

in which

A, D, E, L and $R^{26}$ have the meaning indicated, converting these in a next step by a halogenation into the compounds of the general formulae (Xa) and (Xb)

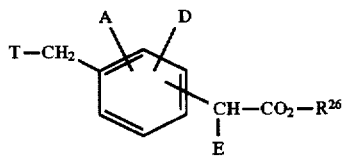

(Xa)

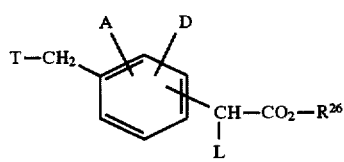

(Xb)

in which

A, D, E, L, T and $R^{26}$ have the meaning indicated, then by reaction with the compounds of the general formula (V) preparing the enantiomerically pure compounds of the general formulae (XIa) and (XIb)

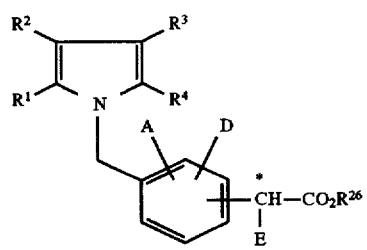

(XIa)

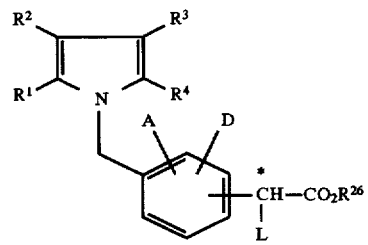

(XIb)

in which

A, D, E, L, $R^1$, $R^2$, $R^3$, $R^4$ and $R^{26}$ have the meaning indicated, and then converting these by hydrolysis into the enantiomerically pure acids of the general formula (II) and optionally by reaction with activating reagents into the corresponding activated carboxylic acid derivatives of the general formula (II).

Additionally, the enantiomerically pure acids of the formula (II) can be prepared by first converting racemic carboxylic acids of the general formula (XII)

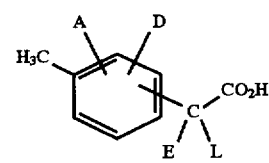

(XII)

in which

A, D, E and L have the meaning indicated above, by reaction with (R)- or (S)-phenylethylamine in inert solvents and subsequent crystallization of the phenethylammonium salts and subsequent hydrolysis of the salts into the enantiomerically pure compounds of the general formula (XIIIa,b)

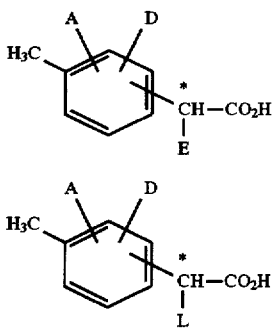
(XIIIa)

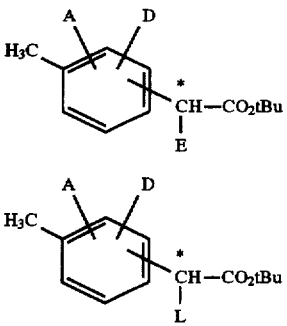
(XIIIb)

in which

A, D, E and L have the meaning indicated above, in a further step with isobutene, in inert solvents and in the presence of acids, preparing the enantiomerically pure esters of the general formula (XIVa,b)

(XIVa)

(XIVb)

in which

A, D, E and L have the meaning indicated above, as described above converting by a halogenation into the enantiomerically pure compounds of the general formula (XVa,b)

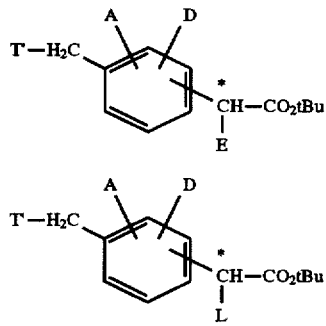
(XVa)

(XVb)

in which

A, D, T, E and L have the meaning indicated above, and by reaction with the compounds of the general formula (V) converting into the enantiomerically pure esters of the general formula (XVIa,b)

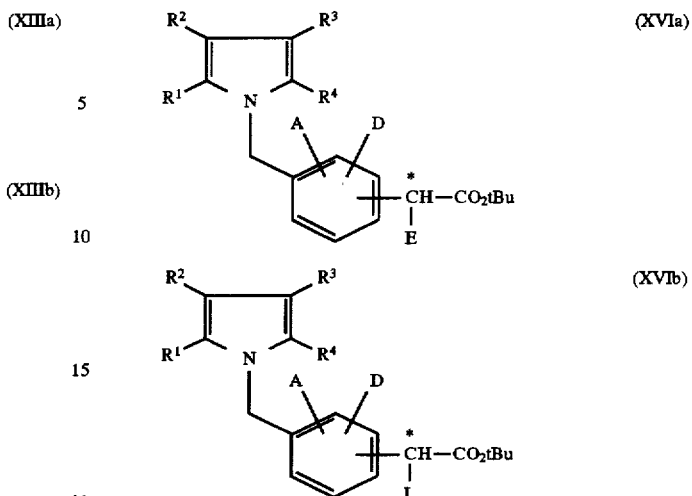

in which

A, D, E, L, $R^1$, $R^2$, $R^3$ and $R^4$ have the meaning indicated above, and in the last steps, as described at the beginning, preparing the corresponding enantiomerically pure acids and activated derivatives.

Suitable solvents for the processes are customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoramide, acetonitrile, acetone or nitromethane. It is also possible to use mixtures of the solvents mentioned. Dimethylformamide, toluene and tetrahydrofuran are preferred.

Bases which can be employed for the processes according to the invention are in general inorganic or organic bases. These preferably include alkali metal hydroxides such as, for example, sodium hydroxide or potassium hydroxide, alkaline earth metal hydroxides such as, for example, barium hydroxide, alkali metal carbonates and hydrogen carbonates such as sodium carbonate, sodium hydrogen carbonate or potassium carbonate, alkaline earth metal carbonates such as calcium carbonate, or alkali metal or alkaline earth metal alkoxides such as sodium or potassium methoxide, sodium or potassium ethoxide or potassium tert-butoxide, or organic amines (trialkyl($C_1$–$C_6$)amines) such as triethylamine, or heterocycles such as 1,4-diazabicyclo[2.2.2]octane (DABCO), 1,8-diazabicyclo[5.4.0]undec-7-ene (DBU, pyridine, diaminopyridine, methylpiperidine or morpholine. It is also possible to employ as bases alkali metals such as sodium or their hydrides such as sodium hydride. Sodium hydrogen carbonate, potassium carbonate and potassium tert-butoxide, DBU or DABCO are preferred.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide, or dimethyl sulphoxide. Particularly preferably, alcohols such as methanol, ethanol, propanol or isopropanol are used. It is also possible to employ mixtures of the solvents mentioned.

The hydrolysis can optionally also be carried out using acids such as, for example, trifluoroacetic acid, acetic acid, hydrochloric acid, hydrobromic acid, methanesulphonic acid, sulphuric acid or perchloric acid, preferably using trifluoroacetic acid.

The hydrolysis is in general carried out in a temperature range from 0°C. to +100°C., preferably from +20° C. to +80° C.

In general, the hydrolysis is carried out at normal pressure. However, it is also possible to work at reduced pressure or at elevated pressure (e.g. from 0.5 to 5 bar).

When carrying out the hydrolysis, the base is in general employed in an amount from 1 to 3 mol, preferably from 1 to 1.5 mol, relative to 1 mol of the ester. Molar amounts of the reactants are particularly preferably used.

The hydrolysis of tert-butyl esters is in general carried out using acids, such as, for example, hydrochloric acid or trifluoroacetic acid, in the presence of one of the solvents indicated above and/or water or mixtures thereof, preferably with dioxane or tetrahydrofuran.

The general process according to the invention is in general carried out in a temperature range from −30° C. to +200° C., preferably from 80° C. to 150° C.

Suitable conditions for the individual steps of the preparation of enantiomerically pure acids are preferably the following:

The preparation of the compounds of the general formulae (IXa) and (IXb) is preferably carried out in dimethylformamide and potassium tert-butoxide in a temperature range from −10° C. to +10° C.

The halogenation of the compounds of the general formulae (Xa) and (Xb) is carried out in chlorobenzene using 1,3-dibromo-5,5-dimethylhydantoin in the presence of azobisisobutyronitrile in a temperature range from 0° C. to 110° C.

The reaction to give the compounds of the general formulae (XIa) and (XIb) is carried out under a protective gas atmosphere in dimethylformamide and potassium tert-butoxide in a temperature range from 0° C. to 30° C.

The hydrolysis of the compounds of the general formulae (XIa) and (XIb) can be carried out as described above, the system HBr/formic acid being particularly preferred. The hydrolysis is carried out in a temperature range from 20° C. to 100° C.

The reaction of the compounds of the general formula (XII) is carried out using methylene chloride under reflux.

Suitable activating reagents are preferably trifluoromethanesulphonyl chloride, mesyl chloride, oxalyl chloride and thionyl chloride. Thionyl chloride is particularly preferred.

The reaction to give the compounds of the general formulae (XIVa) and (XIVb) in the first step is preferably carried out in tetrahydrofuran and triethylamine, in the second step in the system water/hydrochloric acid. The reaction is carried out in a temperature range from 30° C. to 70° C.

The acid employed for the preparation of the compounds of the general formulae (XVa) and (XVb) according to the invention is particularly preferably concentrated sulphuric acid. The preparation is carried out using methylene chloride.

In the further working-up step, potassium carbonate is employed as the base. The reaction is carried out in a temperature range from 0° C. to +20° C., particularly preferably at 10° C.

The halogenation of the compounds of the general formulae (XVa) and (XVb) is carried out using N-bromosuccinimide in methylene chloride in the presence of azobisisobutyronitrile.

In general, the base is employed in an amount from 0.05 mol to 10 mol, preferably from 1 mol to 2 mol, in each case relative to 1 mol of the compounds of the general formulae (IV), (VIIIa), (VIIIb), (XIa), (XIb), (XIVa) and (XIVb).

The processes according to the invention are in general carried out at normal pressure. However, it is also possible to carry out the processes at elevated pressure or at reduced pressure (e.g. in a range from 0.5 to 5 bar).

The compounds of the general formula (III) are known per se.

The compounds of the general formulae (IV), (VIIIa) and (VIIIb) are known or can be prepared in analogy to known methods.

The compounds of the general formula (V) are known in some cases or are new and can then be prepared, however, in analogy to published methods.

The compounds of the general formula (VII) are new as a species and are prepared from the corresponding acid.

The enantiomerically pure compounds of the general formulae (IXa) and (IXb) are new with the exception of X =CH-isopropyl and can be prepared as described above.

The compounds of the general formulae (Xa), (Xb), (XIa), (XIb) and (XII) are new and can be prepared as described above.

The compounds of the general formula (XIIIa), (XIIIb), (XIVa) and (XIVb) are known in some cases or can be prepared by customary methods.

The enantiomerically pure compounds of the general formulae (XVa), (XVb) (XVIa) and (XVIb) are new and can be prepared as described above.

The compounds of the general formula (VI) are new and can be prepared as described above.

The compounds of the general formula (I) according to the invention have an unforeseeable spectrum of pharamacological action.

They can be used as active compounds in medicaments for the reduction of changes to vessel walls and for the treatment of coronary heart disorders, cardiac insufficiency, brain function disorders, ischaemic brain disorders, apoplexy, circulatory disorders, microcirculation disorders and thromboses.

Furthermore, the proliferation of smooth muscle cells plays a decisive part in the occlusion of vessels. The compounds according to the invention are suitable for inhibiting this proliferation and thus for preventing atherosclerotic processes.

The compounds according to the invention are distinguished by a lowering of the ApoB-100-associated lipoproteins (VLDL and its degradation products, such as, for example, LDL), of ApoB-100, of triglycerides and of cholesterol. They thus have useful pharmacological properties which are superior in comparison with the prior art.

Surprisingly, the action of the compounds according to the invention consists first of a reduction or complete inhibition of the formation and/or the release of ApoB-100-associated lipoproteins from liver cells, which results in a lowering of the VLDL plasma level. This lowering of VLDL must be accompanied by a lowering of the plasma levels of ApoB-100, LDL, triglycerides and of cholesterol; thus simultaneously several of the abovementioned risk factors are lowered which are involved in vascular wall changes.

The compounds according to the invention can therefore be employed for the prevention and treatment of atherosclerosis, obesity, pancreatitis and constipation.

1. Inhibition of the release of ApoB-100-associated lipoproteins

The test for detecting the inhibition of the release of ApoB-100-associated lipoproteins from liver cells was carried out in vitro using cultured liver cells, preferably using cells of the human line HepG2. These cells are cultured under standard conditions in medium for the culture of eucaryotic cells, preferably in RPMI 1640 with 10% foetal calf serum. HepG2 cells synthesize and secrete into the culture supernatant ApoB-100-associated lipoprotein particles which in principle are constructed similarly to the VLDL and LDL particles which are to be found in the plasma.

These particles can be detected using an immunoassay for human LDL. This immunoassay is carried out using antibodies which have been induced in rabbits against human LDL under standard conditions. The anti-LDL antibodies (rabbit anti-LDL-Ab) were purified by affinity chromatography on an immunosorbent using human LDL. These purified rabbit anti-LDL-Ab are adsorbed on the surface of plastic. Expediently, this adsorption takes place on the plastic surface of microtitre plates having 96 depressions, preferably on MaxiSorp plates. If ApoB-100-associated particles are present in the supernatant of Hep-G2 cells, these can bind to the insolubilized rabbit anti-LDL-Abs, and an imunune complex results which is bound to the plastic surface. Unbound proteins are removed by washing. The immune complex on the plastic surface is detected using monoclonal antibodies which have been induced against human LDL under standard conditions and purified. These antibodies were conjugated to the enzyme peroxidase. Peroxidase converts the colourless substrate TMB into a coloured product in the presence of $H_2O_2$. After acidification of the reaction mixture with $H_2SO_4$, the specific light adsorption at 450 nm is determined, which is a measure of the amount of ApoB-100-associated particles which have been secreted into the culture supernatant by the HepG2 cells.

Surprisingly, the compounds according to the invention inhibit the release of the ApoB-100-associated particles. The $IC_{50}$ value indicates at which substance concentration the light adsorption is inhibited by 50% in comparison with the control (solvent control without substance).

| Ex. No. | ApoB $IC_{50}$ [nM] |
|---|---|
| 2 | 1.1 |
| 6 | 0.8 |
| 10 | 1.0 |
| 16 | 8.9 |
| 26 | 1.8 |

2. Determination of VLDL secretion in vivo in the hamster

The effect of the test substances on VLDL secretion in vivo is investigated in the hamster. To do this, golden hamsters are anaesthetized with Ketavet (83 mg/kg s.c.) and Nembutal (50 mg/kg i.p.) after premedication with atropine (83 mg/kg s.c.). When the animals have become reflex-free, the jugular vein is exposed and cannulated. 0.25 ml/kg of a 20% strength solution of Triton WR-1339 in physiological saline solution is then administered. This detergent inhibits the lipoprotein lipase and this leads to a rise in the triglyceride level on account of a lack of catabolism of secreted VLDL particles. This triglyceride rise can be used as a measure of the VLDL secretion rate. Blood is taken from the animals before and one and two hours after administration of the detergent by puncture of the retroorbital venous plexus. The blood is incubated for two hours at room temperature, then overnight at 4° C. in order to end clotting completely.

It is then centrifuged for 5 minutes at 10,000 g. In the serum thus obtained, the triglyceride concentration is determined with the aid of a modified commercially available enzyme test (Merckotest® triglyceride No. 14354). 100 µl of serum are treated with 100 µl of test reagent in 96-hole plates and incubated at room temperature for 10 minutes. The optical density is then determined in an automatic plate-reading apparatus (SLT spectra) at a wavelength of 492 nm. Serum samples having too high a triglyceride concentration are diluted with physiological saline solution. The triglyceride concentration contained in the samples is determined with the aid of a standard curve measured in parallel. In this model, test substances are administered either intravenously immediately before administration of the detergent or orally or subcutaneously before initiation of the anaesthesia.

3. Inhibition of intestinal triglyceride absorption in vivo (rats)

The substances which are to be investigated for their triglyceride absorption-inhibiting action in vivo are administered orally to male Wistar rats having a body weight of between 170 and 230 g. For this purpose, the animals are divided into groups of 6 animals 18 hours before substance administration and the feed is then withdrawn from them. Drinking water is available to the animals ad libitum. The animals of the control groups receive an aqueous tragacanth suspension or a tragacanth suspension which contains olive oil. The tragacanth-olive oil suspension is prepared using an Ultra-Turrax. The substances to be investigated are suspended in a corresponding tragacanth-olive oil suspension, likewise using the Ultra-Turrax, directly before substance administration.

Blood is taken from each rat by puncture of the retroorbital venous plexus before stomach tube application to determine the basal serum triglyceride content. The tragacanth suspensions, the tragacanth-olive oil suspensions without substance (control animals), or the substances, suspended in a corresponding tragacanth-olive oil suspension, are then administered to the fasting animals using a stomach tube. Further taking of blood to determine the postprandial serum triglyceride rise is as a rule carried out 1, 2 and 3 hours after stomach tube application.

The blood samples are centrifuged and after coagulation of the serum the triglycerides are determined photometrically using an EPOS analyzer 5060 (Eppendorf Ger ätebau, Netheler & Hinz GmbH, Hamburg). The determination of the triglycerides is carried out completely enzymatically using a commercially available UV test.

The postprandial serum triglyceride rise is determined by subtraction of the triglyceride preliminary value of each animal from its corresponding postprandial triglyceride concentrations (1, 2 and 3 hours after administration).

The differences (in mmol/l) at each time (1, 2 and 3 hours) are calculated in groups as means, and the mean values of the serum triglyceride rise ($\Delta TG$) of the substance-treated animals is compared with the animals which only received the tragacanth-oil suspension.

The serum triglyceride course of the control animals which only received tragacanth is also calculated. The substance effect at each time (1, 2 or 3 hours) is determined as follows and indicated in $\Delta\%$ of the oil-loaded control.

$$\Delta\% \text{ triglyceride rise} = \frac{\Delta TG_{substance} - \Delta TG_{tragacanth\ control}}{\Delta TG_{oil\ loading} - \Delta TG_{tragacanth\ control}} \times 100$$

Effect of 1, 3 or 10 mg of test substance/kg of body weight p.o. on the triglyceride rise ($\Delta\%$) 2 h after a triglyceride loading in the serum of fasting rats. The serum triglyceride rise of fat-loaded control animals relative to the serum triglyceride level of tragacanth control animals corresponds to 100%. n=6 animals per group.

|  | Serum triglyceride rise in % (2 h pp) |
|---|---|
| Triglyceride loading | 100 |
| Tragacanth control | 0 |

Statistical assessment is carried out using Student's t-test after prior checking of the variances for homogeneity.

Substances which at one time statistically significantly (p<0.05) decrease the postprandial serum triglyceride rise by at least 30%, compared with that of the untreated control group, are regarded as pharmacologically active.

4. Inhibition of VLDL secretion in vivo (rat)

The action of the test substances on VLDL secretion is also investigated in the rat. To do this, Triton WR-1339 (2.5 mg/kg), dissolved in physiological saline solution, is administered intravenously into the tail vein of rats of body weight 500 mg/kg. Triton WR-1339 inhibits lipoprotein lipase and thus leads by inhibition of VLDL catabolism to a rise in the triglyceride and cholesterol level. These rises can be used as a measure of the VLDL secretion rate.

Blood is taken from the animals before and two hours after administration of the detergent by puncture of the retroorbital venous plexus. The blood is incubated at room temperature for 1 h for coagulation and the serum is obtained by centrifugation at 10 000 g for 20 s. The triglycerides are then determined photometrically at a wavelength of 540 nm by means of a commercially available coupled enzyme test (Sigma Diagnostics®, No. 339). Measurement is carried out with the aid of a likewise coupled enzyme test (Boehringer Mannheim®, No. 1442350) at a wavelength of 546 nm. Samples having triglyceride and cholesterol concentrations which exceed the measuring range of the methods are diluted with physiological saline solution. The determination of the respective serum concentrations is carried out with the aid of standard series measured in parallel. Test substances are administered orally, intravenously or subcutaneously immediately after the Triton injection.

The invention additionally relates to the combination of pyridazino-, pyrimido-, pyrazino- and triazino-indoles of the general formula (I) with a glucosidase and/or amylase inhibitor for the treatment of familial hyperlipidaemias, of obestiy (adiposity) and of diabetes mellitus. Glucosidase and/or amylase inhibitors in the context of the invention are, for example, acarbose, adiposine, voglibose, miglitol, emiglitate, MDL-25637, camiglibose (MDL-73945), tendamistate, AI-3688, trestatin, pradimicin-Q and salbostatin.

The combination of acarbose, miglitol, emiglitate or voglibose with one of the abovementioned compounds of the general formula (I) according to the invention is preferred.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this context, the therapeutically active compound should in each case be present in a concentration of approximately 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, if water is used as a diluent, organic solvents can optionally be used as auxiliary solvents.

Administration is carried out in a customary manner, preferably orally or parenterally, in particular perlingually or intravenously.

In the case of parenteral administration, solutions of the active compound using suitable liquid excipient materials can be employed.

In general, it has proved advantageous in the case of intravenous administration to administer amounts of approximately 0.001 to 1 mg/kg, preferably approximately 0.01 to 0.5 mg/kg, of body weight to achieve effective results, and in the case of oral administration the dose is approximately 0.01 to 20 mg/kg, preferably 0.1 to 10 mg/kg, of body weight.

In spite of this, if appropriate it may be necessary to deviate from the amounts mentioned, namely depending on the body weight or on the type of administration route, on individual behaviour towards the medicament, the manner of its formulation and the time or interval at which administration takes place. Thus, in some cases it may be adequate to manage with less than the abovementioned minimum amount, while in other cases the upper limit mentioned has to be exceeded. In the case of the administration of relatively large amounts, it may be advisable to divide these into several individual doses over the course of the day.

Abbreviations used:
Ac=acetyl
AIBN=azobisisobutyronitrile
Bn=benzyl
Bz=benzoyl
cDec=cyclodecyl
CDI=N-(3-dimethylaminopropyl)-N-ethylcarbodiimide hydrochloride
cDodec=cyclododecyl
cHept=cycloheptyl
cHex=cyclohexyl
cNon=cyclononyl
cOct=cyclooctyl
cPent=cyclopentyl
cPr=cyclopropyl
18-Crown-6=1,4,7,10,13,16-hexaoxacyclooctadecane
DCC=dicyclohexylcarbodiimide
DDQ=2,3-dichloro-5,6-dicyano-1,4-benzoquinone
dia=diastereomer
dia A=diastereomer having the larger $R_f$
dia B=diastereomer having the smaller $R_f$
DMAP=4-(N,N-dimethylamino)pyridine
DME=1,2-dimethoxyethane
DMF=N,N-dimethylformamide
DMSO=dimethyl sulphoxide
ent=enantiomer
Et=ethyl
HOBT=1-hydroxy-1H-benzotriazole
iBu=isobutyl
iPent=isopentyl
iPr=isopropyl
Me=methyl
Ment=menthyl
Mes=mesyl
NBS=N-bromosuccinimide
nBu=normal butyl
nHex=normal hexyl
nPent=normal pentyl
nPr=normal propyl
Ph=phenyl
PPA=polyphosphoric acid pTol=paratolyl
pTos=paratosyl
rac=racemate
sBu=secondary butyl
tBu=tertiary butyl
TFA=trifluoroacetic acid
THF=tetrahydrofuran
TMS=tetramethylsilane The solvent mixtures used:

| Solvent | Symbol |
|---|---|
| Petroleum ether:ethyl acetate = 20:1 | A |
| Petroleum ether:ethyl acetate = 2:1 | B |
| Petroleum ether:ethyl acetate = 5:1 | C |
| Dichloromethane:ethanol = 20:1 | D |
| Petroleum ether:ethyl acetate = 1:1 | B |
| Dichloromethane:ethanol = 50:1 | F |
| Dichloromethane | G |
| Petroleum ether:methyl acetate = 9:1 | H |
| Dichloromethane:methanol = 20:1 | I |
| Petroleum ether:ethyl acetae = 4:1 | J |
| Dichloromethane:ethanol = 10:1 | K |
| Dichloromethane:methanol = 100:3 | L |
| Toluene | M |
| Toluene:ethyl acetate = 9:1 | N |
| Toluene:ethyl acetate = 2:1 | O |
| Petroleum ether:ethyl acetate = 10:1 | P |
| Petroleum ether:ethyl acetate = 20:1 | Q |
| Petroleum ether | R |
| Petroleum ether:ethyl acetate = 1:2 | S |
| Cyclohexane:ethyl acetate = 1:2 | T |
| Cyclohexane:ethyl acetate = 1:4 | U |

STARTING COMPOUNDS

EXAMPLE I
Methyl 4-tolyl-acetate

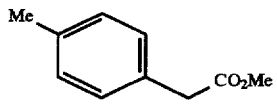

300 g (1.998 mol) of 4-tolyl-acetic acid are dissolved in 2.5 l of methanol, and the solution is stirred with 100 ml of conc. sulphuric acid and boiled under reflux for 2.5 h. A total of 430 g (5.1 mol) of sodium hydrogencarbonate are gradually added to this mixture (evolution of carbon dioxide!), the methanol is largely evaporated in vacuo, the residue is partitioned between water and dichloromethane and the aqueous phase is extracted with dichloromethane. The combined organic phases are dried with sodium sulphate and freed from the solvent in vacuo. The residue is distilled in a high vacuum.

Yield: 336 g Boiling temperature: 65° C. (0.5 mbar) $R_f$=0.81 (toluene:ethyl acetate =2:1)

EXAMPLE II
Ethyl 4-tolyl-acetate

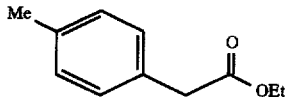

Starting from 4-tolyl-acetic acid, ethyl 4-tolyl-acetate is prepared analogously to the procedure of Example I.
$R_f$=0.43 (A)

EXAMPLE III
tert-Butyl 4-methylphenylacetate

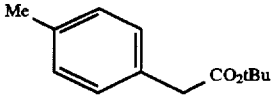

450 g (3 mol) of 4-methylphenylacetic acid, 1.13 l (12 mol) of tert-butanol and 90 g (0.74 mol) of dimethylaminopyridine are dissolved in 2 l of dichloromethane. After addition of 680 g (3.3 mol) of dicyclohexylcarbodiimide, dissolved in 400 ml of dichloromethane, the mixture is stirred at 25° C. for 20 hours. The precipitated urea is filtered off with suction and washed with 200 ml of dichloromethane, and the organic phase is washed twice each with 500 ml of 2M hydrochloric acid and water. The organic phase is dried with sodium sulphate, concentrated and distilled.

Yield: 408 g (66%) Boiling point: 73°–78° C. (0.2 mm Hg)

EXAMPLE IV
tert-Butyl 2(R/S)-2-cyclopentyl-2-(4-methylphenyl)acetate

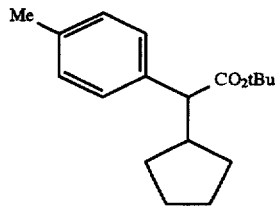

33.5 g (0.3 mol) of potassium tert-butoxide are initially introduced at 0° C. into 100 ml of DMF with exclusion of moisture, and 51.6 g (0.25 mol) of the compound from Example III in 250 ml of DMF are added dropwise. The mixture is stirred at 0° C. for 30 min, 32.2 ml (0.3 mol) of cyclopentyl bromide in 150 ml of DMF are added dropwise at 5°–15° C. and the mixture is stirred at 25° C. for 20 h. After concentrating, the residue is partitioned between water/diethyl ether, and the ether phase is dried over sodium sulphate and concentrated. The product crystallizes out.

Yield: 67 g (97.5%); Melting point: 51°–53° C.

TABLE I

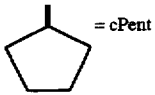

| Ex. No. | —X | —Y | a) M.p. (°C.)<br>b) $R_f$ (solvent) | Spectra | Starting material from Ex. No. |
|---|---|---|---|---|---|
| V | —CH$_3$ = Me | —C(CH$_3$)$_3$ = tBu | b) 0.71 (M) | | III |
| VI | —C$_2$H$_5$ = Et | tBu | b) 0.67 (M) | | III |
| VII | —CH$_2$CH$_2$CH$_3$ = nPr | tBu | b) 0.69 (M) | | III |
| VIII | —CH(CH$_3$)$_2$ = iPr | Me | b) 0.86 (O) | | I |
| IX | —CH(CH$_3$)$_2$ = iPr | tBu | | | III |
| X | —CH$_2$CH$_2$CH$_2$CH$_3$ = nBu | tBu | b) 0.74 (M) | | III |
| XI | —CH$_2$CH(CH$_3$)$_2$ = iBu | tBu | b) 0.70 (M) | | III |
| XII | —CH$_2$CH$_2$CH$_2$CH$_2$CH$_3$ = nPent | tBu | | | III |
| XIII | —CH$_2$CH$_2$—CH(CH$_3$)$_2$ = iPent | tBu | b) 0.54 (P) | | III |
| XIV | —CH(CH$_2$CH$_3$)$_2$ | tBu | | MS: 276 (M$^+$, 4%) | III |
| XV | —CH$_2$CH$_2$CH$_2$CH$_2$CH$_2$CH$_3$ = nHex | tBu | b) 0.75 (M) | | III |
| XVI | —CH$_2$CH(CH$_2$CH$_3$)$_2$ | tBu | | MS: 290 (M$^+$, 1%) | III |
| XVII | 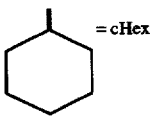 = cPent | Me | b) 0.59 (P) | | I |
| XVIII | 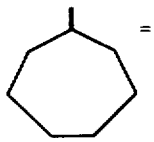 = cHex | Me | b) 0.62 (Q) | | I |
| XIX | cHex | tBu | b) 0.72 (M) | | III |
| XX | 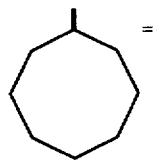 = cHept | Me | b) 0.57 (M) | | I |
| XXI | cHept | tBu | b) 0.67 (M) | | III |
| XXII | 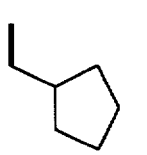 = cOct | tBu | b) 0.77 (M) | | III |
| XXIII | | tBu | b) 0.86 (Q) | | III |

TABLE I-continued

[Structure: 4-methylphenyl-CH(X)-C(=O)-O=Y]

| Ex. No. | —X | —Y | a) M.p. (°C.) b) R$_f$(solvent) | Spectra | Starting material from Ex. No. |
|---|---|---|---|---|---|
| XXIV | CH$_2$-cyclohexyl | tBu | | | III |

TABLE II

[Structure: 4-methylphenyl-X-C(=O)-O—Y]

| Ex No. | —X— | —Y | a) M.p. (°C.) b) R$_f$(solvent) | Spectra | Starting material from Ex. No. |
|---|---|---|---|---|---|
| XXV | C(CH$_3$)$_2$ | tBu | b) 0.68 (F) | | III |
| XXVI | C(CH$_2$CH$_3$)$_2$ | tBu | b) 0.32 (R) | | III |
| XXVII | C(CH$_2$CH$_2$CH$_3$)$_2$ | tBu | b) 0.84 (B) | | III |
| XXVIII | C(CH$_2$CH$_2$CH$_2$CH$_3$)$_2$ | tBu | b) 0.82 (C) | | III |
| XXIX | cyclopentylidene | tBu | b) 0.23 (R) | | III |
| XXX | cyclohexylidene | tBu | b) 0.21 (R) | | III |
| XXXI | cycloheptylidene | tBu | b) 0.26 (R) | | III |

EXAMPLE XXXII tert-Butyl 2(R/S)-2-(4-bromomethyl-phenyl)-2-cyclopentyl-acetate

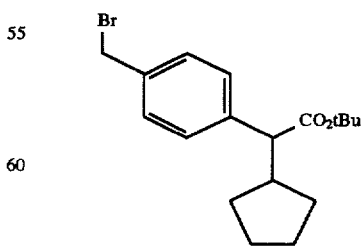

27.4 g (0.1 mol) of the compound from Example IV are dissolved in 200 ml of carbon tetrachloride and the solution is heated to boiling. After addition of 0.82 g of azobisisobutyronitrile, 18.7 g (0.105 mol) of N-bromosuccinimide are added in portions and the mixture is then refluxed for 1 h, cooled to 0° C. and the succinimide is filtered off. After concentrating the filtrate, the product precipitates. It is washed with petroleum ether (40/60) and dried.

Yield: 20 g (57%)
Melting point: 73°–76° C.

The racemic compounds of Table III are prepared analogously to the procedure of Example No. XXXII:

TABLE III

| Ex. No. | —X | —Y | a) M.p. (°C.) b) $R_f$(solvent) | Spectra | Starting material from Ex. No. |
|---|---|---|---|---|---|
| XXXIII | —H | Me | | | I |
| XXXIV | —H | tBu | | | III |
| XXXV | Me | tBu | b) 0.78 (M) | | V |
| XXXVI | Et | tBu | b) 0.75 (M) | | VI |
| XXXVII | nPr | tBu | b) 0.80 (M) | | VII |
| XXXVIII | iPr | Me | b) 0.78 (G) | | VIII |
| XXXIX | iPr | tBu | | | IX |
| XL | nBu | tBu | b) 0.82 (M) | | X |
| XLI | iBu | tBu | b) 0.86 (G) | | XI |
| XLII | nPent | tBu | b) 0.73 (H) | | XII |
| LIII | —CH2-cyclopentyl | tBu | b) 0.58 (A) | | XXIII |
| LIV | —CH2-cyclohexyl | tBu | | | XXIV |

TABLE IV

| Ex. No. | X | —Y | a) M.p. (°C.) b) $R_f$(solvent) | Spectra | Starting material from Ex. No. |
|---|---|---|---|---|---|
| LV | C(CH3)2 | tBu | b) 0.68 (F) | | XXV |
| LVI | C(CH2CH3)2 | tBu | b) 0.38 (Q) | | XXVI |
| LVII | C(CH2CH2CH3)2 | tBu | b) 0.84 (B) | | XXVII |
| LVIII | C(CH2CH2CH2CH3)2 | tBu | b) 0.82 (C) | | XXVIII |
| LIX | cyclopentylidene | tBu | | MS: 356, 358 ([M+NH4]+; 9%, 11%) | XXIX |

TABLE IV-continued

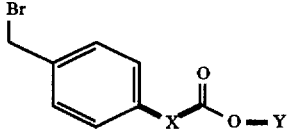

| Ex. No. | X | a) M.p. (°C.)<br>—Y  b) $R_f$(solvent) | Spectra | Starting material from Ex. No. |
|---|---|---|---|---|
| LX | 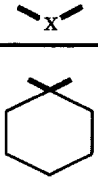 | tBu | MS: 370, 372<br>([M + NH$_4$]$^+$; 5%,<br>5%) | XXX |
| LXI |  | tBu  b) 0.47 (Q) | | XXXI |

EXAMPLE LXII 1,3-Dimethyl-5-nitro-6-[2-(pyrrolidin-1-yl)-cyclohexen-1-yl]-pyrimidine-2,4(1 H, 3H)-dione

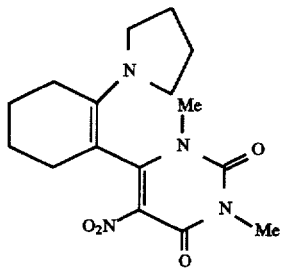

107 g (0.487 mol) of 6-chloro-1,3-dimethyl-5-nitro-pyrimidine-2,4(1H,3H)-dione [J. Clark and I. W. Southon, J. Chem. Soc. Perkin Trans. I, 1814 (1974)] are dissolved in 700 ml of anhydrous DMF and the solution is stirred at 20° C. with 81.8 g (0.974 mol) of sodium hydrogencarbonate and 73.66 g (0.487 mol) of 1-(cyclohexan-1-yl)-pyrrolidine. After 20 hours, the reaction mixture is stirred into ether and aqueous buffer of pH=7 (Merck). By addition of dichloromethane, the phases are separated, and the organic phase is dried with magnesium sulphate and evaporated.

Yield: 110 g (0.329 mol); $R_f$=0.34 (F); MS (DCI/NH$_3$): m/z=335 (26%, [M+H]$^+$).

EXAMPLE LXIII 1,3-Dimethyl-1,5,6,7,8,9-hexahydro-pyrimido[5,4-b]indole-2,4-dione

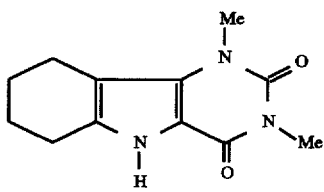

36.6 g; (0.109 mmol) of the compound from Example LXII are dissolved in 1.57 l of ethyl acetate and methanol and reduced on 36 g of hydrogenation catalyst (5% palladium on animal carbon) at 20° C. and an H$_2$ pressure of about 1 bar. After an initial temperature rise to about 30° C., the reaction mixture is filtered off with suction through a Seitz filter 6 hours after the start of the reaction and the filtrate is evaporated. The crude product is stirred successively with methanol, aqueous buffer of pH=2 (Merck) and water, filtered off with suction in each case and finally dried in vacuo over phosphorus pentoxide (yield: 9.84 g (42.2 mmol)).

The methanolic solution is evaporated, and the material obtained is added to the combined aqueous phases and extracted with diethyl ether. The organic phase is evaporated and again stirred with methanol and water. After filtering off with suction and vacuum drying over phosphorus pentoxide, a further 0.22 g (0.9 mmol) of product is obtained.

The hydrogenation catalyst residues are boiled with dichloromethane and methanol and filtered off with suction. The evaporated filtrate is treated as above and after drying yields 0.81 g (3.5 mmol) of the title compound.

$R_f$=0.29 (D) MS (DSI/NH$_3$): m/z=234(100%,[M+H]$^+$).

EXAMPLE LXIV 1,3-Dimethyl-1,5-dihydro-pyrimido[5,4-b]indole-2,4-dione

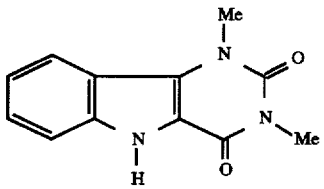

5.0 g (22.4 mmol) of the compound from Example LXIII are reacted at reflux temperature for a total of 42.5 hours with 5 g of palladium (5% strength on animal carbon) and 7.5 ml of diethyl fumarate in 40 ml of diethylene glycol, the amounts of reagent and solvent mentioned being added once more after 10 and 20 hours. The reaction mixture cooled to 20° C. is treated with 500 ml each of dichloromethane and methanol and heated to reflux. This hot mixture is filtered off with suction through a Seitz filter and the residue is washed with 500 ml of a solvent mixture of diethyl ether, dichloromethane, methanol and ethyl acetate (mixing ratio= 1:1:1:1). The filtrate is evaporated and precipitated with acetone with stirring. The precipitate is filtered off with suction and freed from the residual solvent in a high vacuum.

Yield: 1.9 g (8.3 mmol); R$_f$=0.38 (E); MS (EI): m/z=230 (100%, [M+H]⁺).

EXAMPLE LXV
2,4-Dimethyl-5H-pyrimido[4,5-b]indole

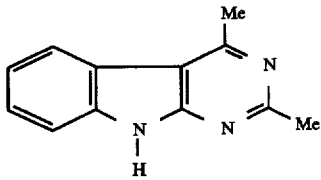

12.1 g (60.0 mmol) of 2,4-dimethyl-6,7,8,9-tetrahydro-5H-pyrimido[4,5-b]indole [(T. D. Duffy and D. G. Wibberley, J. Chem. Soc., Perkin Trans. I, 1921 (1974)] are reacted analogously to the preparation procedure for the compound from Example LXIV to give the title compound already prepared in another way [Y. Kondo, R. Watanabe, T. Sakamoto and H. Yamanaka, Chem. Pharm. Bull., 37, 2933 (1989)].

Yield: 10.1 g (51.2 mmol); R$_f$=0.20 (D); MS (DCI/NH$_3$): m/z=198 (100%, [M+H]⁺).

EXAMPLE LXVI
3-Methoxycarbonyl-indole-2-carboxylic acid

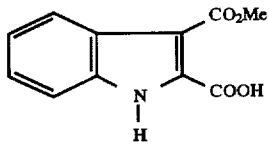

4.24 g (18.2 mmol) of dimethyl indole-2,3-dicarboxylate (Lancaster) are dissolved in 120 ml of methanol and the solution is stirred at 20° C. for 6 hours with 37 ml of 2M aqueous sodium hydroxide solution. After this the mixture is poured onto diethyl ether, dichloromethane and water, adjusted by addition of hydrochloric acid to pH=3, the aqueous phase is extracted again with the solvent mixture, and the combined organic extracts are dried with magnesium sulphate and evaporated to dryness. Yield: 3.98 g. The substance is reacted further without further purification.

R$_f$=0.18 (F); ¹³C—NMR (d$_6$-DMSO, 75 MHz, d$_5$-DMSO): δ=52.67 (Q); 106.81 (S); 113.17 (D); 122.05 (D); 122.76 (D); 125.18 (D); 125.52 (S); 132.48 (S); 135.18 (S); 160.56 (S); 167.91 (S) ppm. MS (EI): m/z =219 (100%, M⁺)

EXAMPLE LXVII
N,N'-Dimethyl-3-methoxycarbonyl-2-indole carbohydrazide

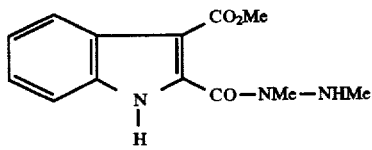

4.84 g (36.4 mmol) of N,N'-dimethylhydrazinium dichloride are dissolved in 60 ml of dichloromethane and the solution is treated successively at 20° C. with 5.1 ml of triethylamine, 3.99 g (18.2 mmol) of the compound from Example LXVI, 2.7 g (20 mmol) of HOBT, 4.01 g (21 mmol) of CDI and 7.6 ml (54.6 mmol) of triethylamine and stirred for 24 hours. If reaction is incomplete [TLC checking using the eluent system dichloromethane:ethanol 20:1], 1.35 g (10 mmol) of HOBT, 2 g (10.5 mmol) of CDI, 2.42 g (18.2 mmol) of N,N'-dimethylhydrazinium dichloride and 3.8 g (27.3 mmol) of triethylamine are added and the solution is stirred for a further 24 hours. The mixture is poured onto buffer of pH=2 (Merck), the aqueous phase is extracted again with dichloromethane and the combined organic phases are dried with magnesium sulphate and evaporated. After chromatographic purification (silica gel 60, Merck, dichloromethane:ethanol; first 50:1, then 20:1, finally 10:1), 3.0 g (11.5 mmol) of the title compound are obtained.

R$_f$=0.34 (D); MS (DCI/NH$_3$): m/z=262 (100%, [M+H]⁺).

EXAMPLE LXVIII
2,3-Dihydro-2,3-dimethyl-5H-pyridazino[4,5-b]indole-1,4-dione

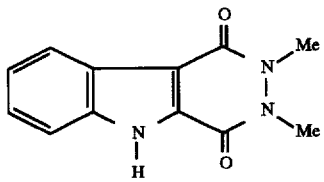

2.1 g (8.0 mmol) of the compound from Example LXVII are stirred at 190° C. for 20 hours in 60 ml of tetralin. After cooling to 20° C., a precipitate is deposited which is filtered off with suction and washed with petroleum ether and dichloromethane. The removal of solvent residues in a high vacuum affords a yield of 1.3 g (5.7 mmol).

R$_f$=0.24 (D) MS (DCI/NH$_3$):m/z=230 (100%, [M+H]⁺).

EXAMPLE LXIX
1,3-Dimethyl-1,9-dihydro-pyrimido[4,5-b]indole-2,4-dione

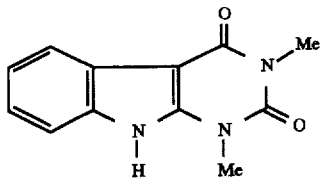

14.8 g (60.1 mmol) of 1,3-dimethyl-6-(N'-phenylhydrazino)-1H-pyrimidine-2,4-dione [S. Senda, K. Hirota and G. N. Yang, Chem. Pharm. Bull. 20, 399 (1982)] are boiled under reflux for 30 minutes in 180 ml of tetralin [S. Senda, K. Hirota and M. Takahashi, J. Chem. Soc., Perkin Trans. I, 503 (1975)]. After cooling to 20° C., a precipitate is deposited which is filtered off with suction and washed with acetone. After drying in a high vacuum, 10.8 g (47.1 mmol) of the title compound are obtained.

R$_f$=0.34 (D); MS (EI):m/z=229 (100%, M⁺)

EXAMPLE LXX
1,1-Dimethyl-ethyl 2-(R/S)-2-cyclopentyl-2-(4-{1,3-dimethyl-1,5-dihydro-2,4-oxo-pyrimido[5,4-b]indol-5-ylmethyl}-phenyl)-acetate

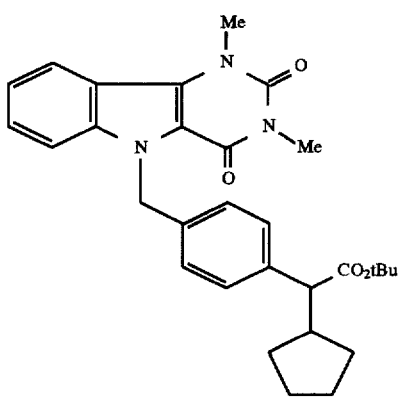

1.00 g (4.36 mmol) of the compound from Example LXIV is stirred with 0.49 g (4.36 mmol) of the potassium alkoxide of 1,1-dimethyl-ethanol in 20 ml of DMF at about 20° C. and, after 20 minutes, the mixture is treated dropwise with a solution of 1.88 g (about 4.4 mmol/about 80% strength material) of 1,1-dimethyl-ethyl 2-(R/S)-2-(4-bromomethyl)-phenyl-2-cyclopentyl-acetate. After about 1 hour, the reaction mixture is poured onto aqueous buffer solution of pH=4 (Merck) and the precipitate which is obtained is filtered off with suction (should a material which cannot be filtered off with suction be formed in this working step, the mixture can also be worked up by extraction). The crude product is purified by chromatography on silica gel 60 (Merck/petroleum ether : ethyl acetate =1:1 to 1:4).

Yield: 0.485 g (0.97 mmol); $R_f$=0.64 (E)

The racemic compounds of Table V are prepared analogously to the procedure of Example LXX:

TABLE V

| Ex. No. | Z | (Absolute configuration) E | $R^{27}$ | a) M.p.(°C.) b) $R_f$ (solvent) | Spectra | Starting material a) Literature b) Marketing company c) Synthesis analogously to/from Ex. No. |
|---|---|---|---|---|---|---|
| LXXI | [structure] | (S) cPent | L-(−)-Ment | b) 0.25 (F) | | c) Ex. No. LXIII |
| LXXII | [structure] | (R + S) cPent | Me | b) 0.40 (D) | | c) Ex. No. LXV |
| LXXIII | [structure] | (R + S) cPent | tBu | b) 0.35 (J) | | c) Ex. No. LXVIII |
| LXXIV | [structure] | (R + S) cPent | tBu | b) 0.27 (B) | MS (FAB): m/z = 524 (6%, [M + Na]+), 501 (44%, M+) | c) Ex. No. LXIX |

TABLE V-continued

[Structure: Z-CH2-C6H4-CH(E)-C(=O)-O-R27]

| Ex. No. | Z | (Absolute configuration) E | R27 | a) M.p.(°C.) b) Rf (solvent) | Spectra | Starting material a) Literature b) Marketing company c) Synthesis analogously to/from Ex. No. |
|---|---|---|---|---|---|---|
| LXXV | [3-(1-methyl-N=C(Me)-) indole, N-Me] | (R + S) iPent | tBu | b) 0.45 (I) | MS (ESI): m/z = 472 (100%, [M + H]+) | c) Ex. No. LXV |
| LXXVI | [pyrrolo-dipyridine with Me groups, N-Me] | (R + S) cPent | tBu | | | c) Ex. No. |
| LXXVII | [pyrrolo-dipyridine isomer with Me groups, N-Me] | (R + S) cPent | tBu | | | c) Ex. No. |
| LXXVIII | [3-(N=N-C(SMe)=N-) indole, N-Me] | (R + S) cPent | tBu | b) 0.27 (F) | | a) G. Doleschall and K. Lempert, Tetrahedron 30, 3997 (1974). |
| LXXIX | [indolo-quinoxaline, N-Me] | (R + S) cPent | tBu | b) 0.57 (U) | | b) Parish |

EXAMPLE LXXX 2-(R/S)-2-Cyclopentyl-2-(4-{1,3 -dimethyl- 1,5-dihydro-2, 4-oxo-pyrimido[5,4-b]indol -5-yl-methyl}-phenyl)-acetic acid

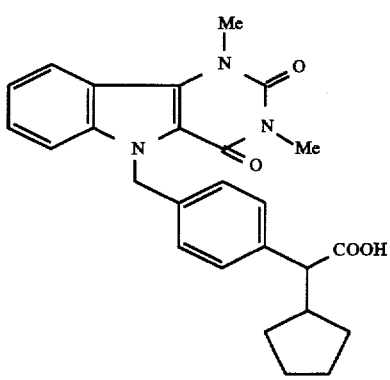

0.479 g (0.95 mmol) of the compound from Example LXX are dissolved in 10 ml of dioxane, and the solution is treated with 0.84 ml of concentrated hydrochloric acid and stirred for 6 hours in a hot bath at 70° C. The reaction mixture is poured onto water, adjusted to a pH of 1.6 using 2M aqueous sodium hydroxide solution, and the precipitate thus obtained is filtered off with suction and washed with water. After drying in a high vacuum over phosphorus pentoxide, 0.377 g (0.885 mmol) of product is obtained.

$R_f$=0.30 (D)

TABLE VI

| Ex. No. | Z | (Absolute configuration) E | a) M.p. (°C.) b) $R_f$ (solvent) | Spectra | Starting material a) Literature b) Marketing company c) Synthesis analogously to/from Ex. No. |
|---|---|---|---|---|---|
| LXXXI | | (R + S) cPent | b) 0.45 (K) | | c) Ex. No. LXXIII |
| LXXXII | | (R + S) cPent | b) 0.23 (F) | | c) Ex. No. LXXIV |
| LXXXIII | | (R + S) iPent | a) 198° C. | MS (ESI): m/z = 416 (100%, [M + H]⁺) | c) Ex. No. LXXV |
| LXXXIV | | (R + S) cPent | a) > 220° C. | MS (ESI/pos.): m/z = 436 ([M + H]⁺, 100%) | c) Ex. No. LXXVI |

TABLE VI-continued

[Structure: 4-(CH2-Z)-phenyl-CH(E)-COOH]

| Ex. No. | Z | (Absolute configuration) E | a) M.p. (°C.) b) R$_f$ (solvent) Spectra | Starting material a) Literature b) Marketing company c) Synthesis analogously to/from Ex. No. |
|---|---|---|---|---|
| LXXXV | [4-Me, 2-Me pyrimido[4,5-b]indol-5-yl-methyl] | (R + S) cPent | | c) Ex. No. LXXVII |
| LXXXVI | [3-(N=N-C(SMe)=N) indol-1-yl] | (R + S) cPent | b) 0.27 (D) | c) Ex. No. LXXVIII |
| LXXXVII | [pyrazino-indole-methyl] | (R + S) cPent | a) >220° C. MS (ESI/pos.): m/z = 436 ([M + H]$^+$, 100%) | c) Ex. No. LXXIX |

EXAMPLE LXXXVIII 2-(R/S)-2-Cyclopentyl-2-[4-{(2,4-dimethyl-5H-pyrimido[4,5-b]indol-5-yl)-methyl}-phenyl]dihydrochloride

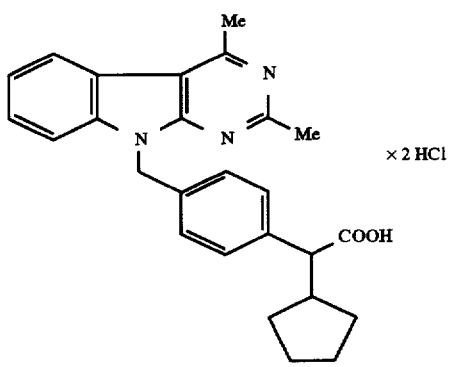

× 2 HCl 4.30 g (10.06 mmol) of the compound from Example LXXII are boiled under reflux for 4 hours with 0.264 g (1 mmol) of 18-crown-6 in 30.2 ml of 1M aqueous potassium hydroxide solution and 40 ml of methanol. After cooling the reaction mixture, 100 ml of water are added for working up and the mixture is extracted with diethyl ether. The aqueous phase is adjusted to a pH of 2 using 1M hydrochloric acid, and the precipitate obtained is filtered off with suction and washed with water. High-vacuum drying over phosphorus pentoxide and potassium hydroxide affords 4.6 g (9.46 mmol) of product.

R$_f$=0.22 (D);

EXAMPLE LXXXIX 2-(S)-2-Cyclopentyl-2-(4-{1,3-dimethyl-1,5,6,7,8,9-hexahydro-2,4-oxo-pyrimido[5,4-b]indol-5-yl-methyl}-phenyl})-acetic acid

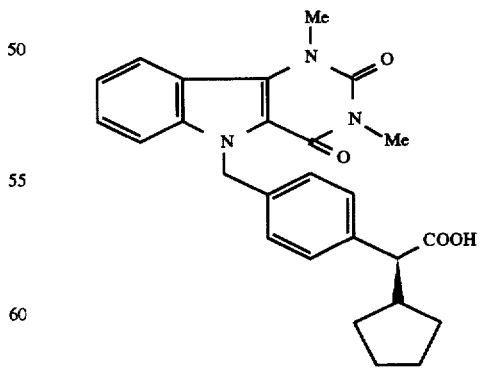

0.98 g (1.7 mmol) of the compound from Example LXXI are boiled under reflux for 1.5 hours in 10 ml of about 40% strength aqueous hydrobromic acid and 20 ml of formic acid. The deep-red reaction mixture is poured onto diethyl ether and water, and the aqueous phase is adjusted to pH=3 with 2M sodium hydroxide solution and extracted again several times with diethyl ether. The combined ethereal extracts are dried with magnesium sulphate and evaporated. After chromatographic purification on silica gel 60 (Merck/ petroleum ether: ethyl acetate=1:1), 0.176 g (0.39 mmol) of product are obtained.

$R_f$=0.18 (S);

PREPARATION EXAMPLES

Example Nos. 1, 2 and 3

2-(R)- and 2-(S)-2-Cyclopentyl-2-(4-{1,3-dimethyl-1,5-dihydro-2,4-oxo-pyrimido-[5,4-b]indol-5-yl-methyl}phenyl)-aceticacidN-(2-hydroxy-1 -(R)-1-phenyl-ethyl)amide

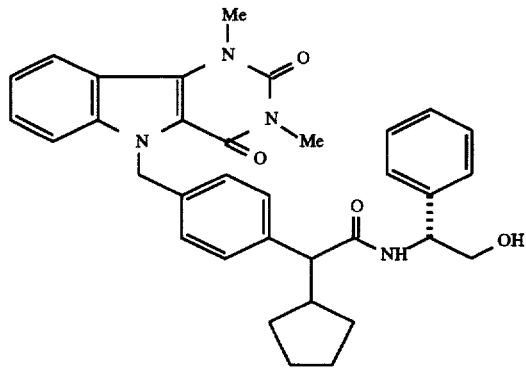

377 mg (0.846 mol) of the compound from Example LXXX are treated at 20° C. with 116 mg (0.846 mmol) of 2-(R)-2-amino-2-phenyl-ethanol, 126 ml (0.93 mmol) of HOBT, 186.5 mg (0.97 mmol) of CDI and 0.234 ml (1.7 mmol) of triethylamine in 20 ml of dichloromethane and the solution is stirred for 20 hours. The reaction mixture is extracted successively with aqueous ammonium chloride solution, aqueous sodium hydrogencarbonate solution and aqueous buffer of pH 0.4 (Merck), dried with magnesium sulphate and evaporated in vacuo.

Yield: 450 mg (0.80 mmol);

Example No. 1: Diastereomer A+B; $R_f$=0.36 (D); MS (FAB): m/z=587 (37%, [M+Na]$^+$),565(100%, {M+H]$^+$).

The diastereomer mixture is separated by chromatography on Kromasil 100 C 18 (55% of a 0.2% strength aqueous trifluoroacetic acid solution +45% acetonitrile).

Example No.2: Diastereomer A [2(S)-diastereomer]:

$^1$H-NMR (d$_6$-DMSO, 200 MHz, TMS) characteristic signals: δ=6.95–7.12 (M, 6H); 7.15–7.26 (M, 3H) ppm.

Example No. 3: diastereomer B [2(R)-diastereomer]:

$^1$H-NMR (d$_6$-DMSO, 200 MHz, TMS) characteristic signals: δ=7.08 (M, 2H); 7.16–7.33 (M, 8H) ppm.

The absolute configurations of the enantiomerically pure carboxylic acids 2-(S)- and 2-(R)-2-{4-[(quinolin-2-yl) methoxy-phenyl}-2-cyclopentyl-acetic acid [EP 509 359] are known, so that the absolute configurations of the amides Ex. No. C1 and Ex. No. C2 prepared therefrom analogously to the procedure for Examples 1 and 2 can be deduced. The $^1$H-NMR spectra of the two diastereomeric products (200 MHz, d$_6$-DMSO, TMS for Example No. C1 and 250 MHz, d$_6$-DMSO, TMS for Example No. C2 (FIG. 1) have significant differences in the aromatic region: the H signals of the phenyl radical of Example No. C1 at about 7.1 ppm (3H) and 7.3 ppm (2H), the H signals of Example No. C2 at about 7.3 ppm (5H). This finding has been applied to the compounds of Examples 2 and 3 and to other derivatives of this type and the absolute and relative configurations indicated thus determined.

TABLE 1

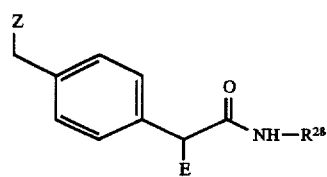

| Ex. No. | Z | E (Absolute configuration) | R$^{28}$ | a) M.p. (°C.) b) R$_f$ (solvent) | Spectra | Starting material a) Literature b) Marketing company c) Synthesis analogously to/from Ex. No. |
|---|---|---|---|---|---|---|
| 4 | 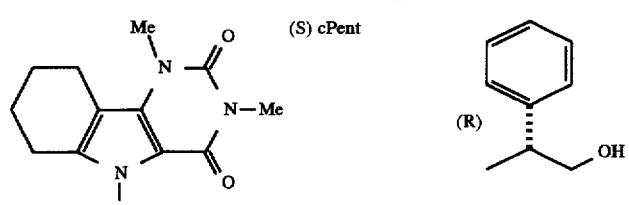 | (S) cPent | (R) phenyl-CH(CH$_3$)-OH | b) 0.29 (D) | | c) Ex. No. LXXXIX |

TABLE 1-continued

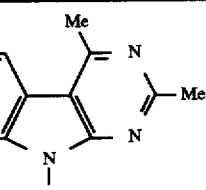

| Ex. No. | Z | (Absolute configuration) E | R²⁸ | a) M.p. (°C.) b) R_f (solvent) | Spectra | Starting material a) Literature b) Marketing company c) Synthesis analogously to/from Ex. No. |
|---|---|---|---|---|---|---|
| 5 | 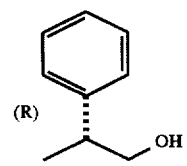 | (R + S) cPent | 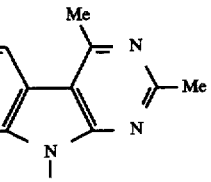 | b) 0.20/0.32 (D) | | c) Ex. No. LXXXVIII |
| 6 | 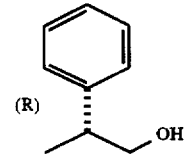 | (S) cPent | 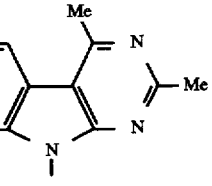 | b) 0.32 (D) | | c) Ex. No. LXXXVIII |
| 7 | 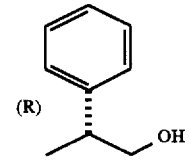 | (R) cPent | 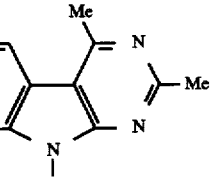 | b) 0.20 (D) | | c) Ex. No. LXXXVIII |
| 8 | 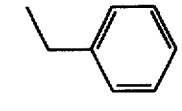 | (R + S) cPent | 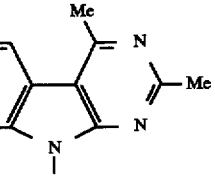 | b) 0.36 (D) | MS (ESI): m/z = 503 (100%, [M + H]⁺) | c) Ex. No. LXXXVIII |
| 9 | 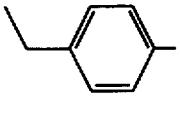 | (R + S) cPent | 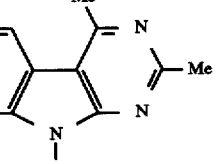 | b) 0.23 (D) | MS (ESI): m/z = 519 (100%, [M + H]⁺) | c) Ex. No. LXXXVIII |
| 10 | 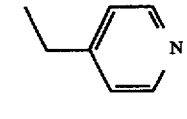 | (R + S) cPent | | b) 0.08 (D) | | c) Ex. No. LXXXVIII |

TABLE 1-continued

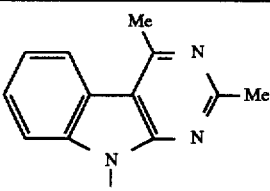

| Ex. No. | Z | (Absolute configuration) E | R28 | a) M.p. (°C.) b) Rf (solvent) | Spectra | Starting material a) Literature b) Marketing company c) Synthesis analogously to/from Ex. No. |
|---|---|---|---|---|---|---|
| 11 | 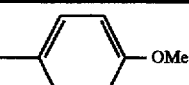 | (R + S) cPent | 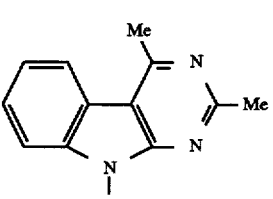 | b) 0.39 (D) | MS (ESI): m/z = 533 (100%, [M + H]+) | c) Ex. No. LXXXVIII |
| 12 | 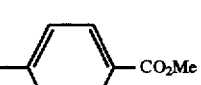 | (R + S) cPent | 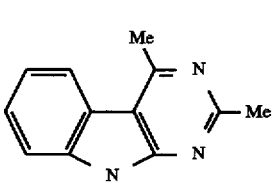 | b) 0.36 (D) | MS (ESI): m/z = 561 (100%, [M + H]+) | c) Ex. No. LXXXVIII |
| 13 | 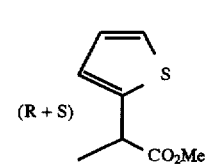 | (R + S) iPent | 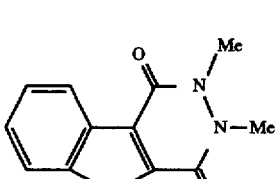 | a) 80° C. b) 0.52 (I) | MS (ESI): m/z = 569 (100%, [M + H]+) | c) Ex. No. LXXXIII |
| 14 | 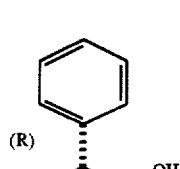 | (R + S) cPent | 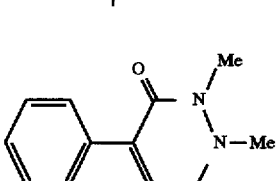 | b) 0.29 (D) | MS (FAB): m/z = 587 (11%, [M + Na]+), 565 (43%, [M + H]+) | c) Ex. No. LXXXI |
| 15 | 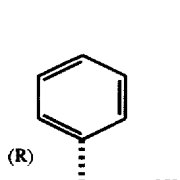 | (S) cPent | 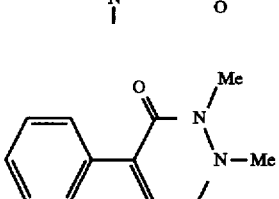 | b) 0.29 (D) | | c) Ex. No. LXXXI |
| 16 | 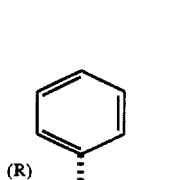 | (R) cPent | | b) 0.29 (D) | | c) Ex. No. LXXXI |

TABLE 1-continued

Structure: 4-(ZCH2)-C6H4-CH(E)-C(=O)-NH-R28

| Ex. No. | Z | (Absolute configuration) E | R28 | a) M.p. (°C.) b) R_f (solvent) | Spectra | Starting material a) Literature b) Marketing company c) Synthesis analogously to/from Ex. No. |
|---|---|---|---|---|---|---|
| 17 | 1-methyl-2-(N-methyl-carbamoyl)-indol-3-yl-carbonyl (with N-Me on carbamoyl) | (R + S) cPent | (R)-CH(CH3)CH2OH, phenyl | b) 0.15 (F) | | c) Ex. No. LXXXII |
| 18 | 1-methyl-2-(N-methyl-carbamoyl)-indol-3-yl-carbonyl | (S) cPent | (R)-CH(CH3)CH2OH, phenyl | b) 0.15 (F) | | c) Ex. No. LXXXII |
| 19 | 1-methyl-2-(N-methyl-carbamoyl)-indol-3-yl-carbonyl | (R) cPent | (R)-CH(CH3)CH2OH, phenyl | b) 0.15 (F) | | c) Ex. No. LXXXII |
| 20 | 4,6-dimethyl-5-methyl-pyrrolo[2,3-b:5,4-b']dipyridinyl | (R + S) cPent | (R)-CH(CH3)CH2OH, phenyl | | | c) Ex. No. LXXXIV |
| 21 | 4,6-dimethyl-5-methyl-pyrrolo[2,3-b:5,4-b']dipyridinyl | (S) cPent | (R)-CH(CH3)CH2OH, phenyl | | | c) Ex. No. LXXXIV |

TABLE 1-continued

| Ex. No. | Z | (Absolute configuration) E | R[28] | a) M.p. (°C.) b) R_f (solvent) | Spectra | Starting material a) Literature b) Marketing company c) Synthesis analogously to/from Ex. No. |
|---|---|---|---|---|---|---|
| 22 | [pyrrolo-pyridine with Me, Me substituents] | (R) cPent | (R)-CH(Ph)-CH(Me)-OH | | | c) Ex. No. LXXXIV |
| 23 | [pyrrolo-pyridine with Me, Me substituents] | (R + S) cPent | (R)-CH(Ph)-CH(Me)-OH | | | c) Ex. No. LXXXV |
| 24 | [pyrrolo-pyridine with Me, Me substituents] | (S) cPent | (R)-CH(Ph)-CH(Me)-OH | | | c) Ex. No. LXXXV |
| 25 | [pyrrolo-pyridine with Me, Me substituents] | (R) cPent | (R)-CH(Ph)-CH(Me)-OH | | | c) Ex. No. LXXXV |
| 26 | [indole with N=N-C(SMe)=N] | (R + S) cPent | (R)-CH(Ph)-CH(Me)-OH | b) 0.37 (D) | MS (FAB): m/z = 552 (100%, [M + H]$^+$) | c) Ex. No. LXXXVI |
| 27 | [indole with fused pyrazine] | (R + S) cPent | (R)-CH(Ph)-CH(Me)-OH | a) 214° C. b) 0.50 (T) | | c) Ex. No. LXXXVII |

EXAMPLE 28

2-(R/S)-2-Cyclopentyl-2-[4-{(2,4-dimethyl-5H-pyrimido[4,5-b]indol-5-yl) methyl}-phenyl-acetic acid N-(4-carboxy-benzyl)-amide dihydrochloride

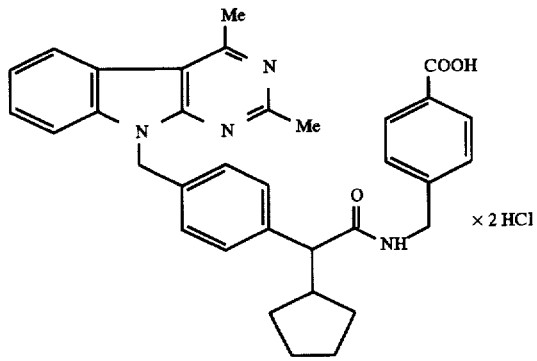

0.35 g (0.62 mmol) of the compound from Example 12 is dissolved in 1 ml of methanol, and the solution is treated with 0.6 ml of 2M aqueous sodium hydroxide solution and boiled under reflux for 2 hours. The cooled reaction mixture is diluted with 100 ml of water and extracted with 2 ml of diethyl ether. After this, the aqueous phase is adjusted to a pH of 2 using 1M aqueous hydrochloric acid and the precipitate which is obtained is filtered off with suction and washed with water. After high-vacuum drying over potassium hydroxide, 0.32 (0.52 mmol) of product is obtained.

$R_f$=0.18 (D); MS (CI): m/z =547 (100%, [M+H]$^+$/without HCl).

EXAMPLE 29, EXAMPLE 30 and EXAMPLE 31

9-(4-(1-(3 -Methyl)butyl-1-1(R/S)-(2-hydroxy-1 -thien-2-yl) ethylaminocarbonyl-4-methyl-pentyl)benzyl-2,4-dimethyl-pyrimido[4,5-b]indole and the racemic diastereomers of 9-(4-(1-(2-hydroxy-1 -thien-2-yl)-ethylaminocarbonyl-4-methyl)-pentyl) benzyl-2,4-dimethyl-pyrimido[4,5-b]indole (29)

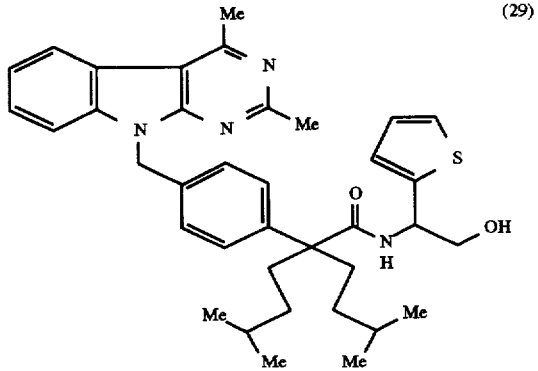

(30) and (31)

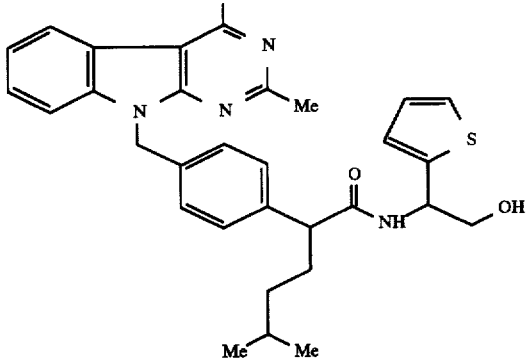

1.47 g (2.58 mmol) of the compound from Example 13 are dissolved in 25 ml of THF and treated dropwise at 0° C. with 5.7 ml of lithium aluminium hydride solution in THF (1M, 5.69 mmol). After stirring at this temperature for about 15 min, the mixture is treated with water and extracted with ethyl acetate, and the organic phase is washed with potassium sodium tartrate solution and dried over sodium sulphate. Chromatography on silica gel using a cyclohexane-ethyl acetate 4:1 mixture afforded three fractions:

Example 29: 300 mg [19%]

Example 30: 146 mg [10%]

Example 31: 57 mg [4%]

PHYSICAL DATA:

EXAMPLE 29:

m.p.: 168° C.; $R_f$=0.53 (U); MS (ESI/POS): 611 ([M+H]$^+$, 100%); $^1$H-NMR (CDCl$_3$,TMS):δ=0.74 –1.06 (m, 16H); 1.46(sept., J=6 Hz, 2H); 1.91(t, broad, J=7.5 Hz, 4H); 2.84 (s, 3H); 3.02 (s, 3H); 3.80 (d, J=5 Hz, 2H); 5.32(dt, J$_1$ =7.5 Hz, J$_2$=5 Hz, 1H); 5.60 –5.72 (m, 3H); 6.74 –6.86 (m, 2H); 7.09 (d, broad, J=5 Hz, 1H); 7.20 –7.48 (m, 7H); 8.10 (d, J=7.5 Hz, 1H) ppm.

EXAMPLE 30:

m.p.: 201° C. $R_f$=0.44 (U) MS (CI, NH$_3$): 541 ([M+H]$^+$, 100%) $^1$H-NMR (CDCl$_3$, TMS): δ=0.81 (d, J=7 Hz, 3H); 0.84 (d, J=7 Hz, 3H); 0.94–1.28 (m, 2H); 1.50 (sept., J=6 Hz, 1H); 1.58–1.82 (m, 1H); 2.00–2.21 (m, 1H); 2.81 (s, 3H); 2.98 (s, 3H); 3.27 (t, J=7.5 Hz, 1H); 3.86 (d, J=5 Hz, 2H); 5.29 (dt, J$_1$=7.5 Hz, J$_2$=5 Hz, 1H); 5.62 (s, 2H); 6.06 (d, J=7.5 Hz, 1H); 6.65–6.84 (m, 2H); 7.05 (d, broad, J=5 Hz, 1H); 7.16–7.50 (m, 7H); 8.08 (d, J=9 Hz, 1H) ppm.

EXAMPLE 31:

m.p.: 194° C. $R_f$=0.36 (U) MS (ESI/POS): 541 ([M+H]$^+$, 100%) $^1$H-NMR (CDCl$_3$, TMS) δ=0.81 (d, J=7 Hz, 3H); 0.83 (d, J=7 Hz, 3H); 0.94–1.22 (m, 2H); 1.40–1.58 (m, 1H); 1.60–1.82 ((m, 1H); 1.98–2.19 (m, 1H); 2.82 (s, 3H); 2.97 (s, 3H); 3.25 (t, J=7.5 Hz, 1H); 3.72–3.86 (m, 2H); 5.31 (dt, J$_1$=7.5 Hz, J$_2$=5 Hz, 1H); 5.62 (s, 2H); 6.08 (d, J=7.5 H, 1H); 6.86–6.96 (m, 2H); 7.12–7.50 (m, 8H); 8.08 (d, J=9 Hz, 1H) ppm.

We claim:
1. Compounds of the formula (I)

in which
R$^1$ and R$^2$, including the double bond connecting them, together form a phenyl ring or a 5- to 8-membered cycloalkene or oxocycloalkene ring,
which is optionally substituted up to 3 times in an identical or different manner by halogen, trifluoromethyl, carboxyl, hydroxyl, by straight-chain or branched alkoxy or alkoxycarbonyl each having up to 6 carbon atoms or by straight-chain or branched alkyl having up to 6 carbon atoms, which for its part can be substituted by hydroxyl or by straight-chain or branched alkoxy having up to 4 carbon atoms,
R$^3$ and R$^4$, including the double bond, together form a radical of the formula in which
R$^7$, R$^8$, R$^9$, R$^{10}$, R$^{11}$, R$^{12}$, R$^{13}$, R$^{14}$, R$^{15}$ and R$^{16}$ are identical or different and denote hydrogen, carboxyl, straight-chain or branched alkoxy, alkylthio, acyl or alkoxycarbonyl each having up to 6 carbon atoms or straight-chain or branched alkyl having up to 6 carbon atoms, which is optionally substituted by hydroxyl, or
R$^1$ and R$^2$, including the double bond, form a pyridyl ring, and
R$^3$ and R$^4$, likewise including the double bond, together form a pyridyl ring, both pyridyl rings optionally being substituted up to 3 times in an identical or different manner by halogen, trifluoromethyl, carboxyl, hydroxyl, by straight-chain or branched alkoxy or alkoxycarbonyl each having up to 6 carbon atoms or by straight-chain or branched alkyl having up to 6 carbon atoms, which for its part is substituted by hydroxyl or by straight-chain or branched alkoxy having up to 4 carbon atoms,
A and D are identical or different and
represent hydrogen, halogen, trifluoromethyl, hydroxyl or straight-chain or branched alkyl or alkoxy each having up to 5 carbon atoms,
E and L are identical or different and
represent hydrogen, cycloalkyl having 3 to 8 carbon atoms or straight-chain or branched alkyl having up to 10 carbon atoms, which is optionally substituted by cycloalkyl having 3 to 6 carbon atoms, or represent phenyl which is optionally substituted by halogen or trifluoromethyl, or
E and L, together with the carbon atom, form a 4-8-membered cycloalkyl ring,
R$^5$ represents phenyl or a 5- to 7-membered saturated or unsaturated heterocycle having up to 3 heteroatoms from the series S, N and/or O, the cycles optionally being substituted up to 3 times in an identical or different manner by nitro, carboxyl, halogen, cyano or by straight-chain or branched alkenyl or alkoxycarbonyl each having up to 6 carbon atoms or by straight-chain or branched alkyl having up to 6 carbon atoms, which is optionally substituted by hydroxyl, carboxyl or by straight-chain or branched alkoxy or alkoxycarbonyl each having up to 6 carbon atoms,
and/or the cycles optionally being substituted by a group of the formula —OR$^{17}$ or —NR$^{18}$R$^{19}$,
in which
R$^{17}$ denotes hydrogen or straight-chain or branched alkyl or alkenyl each having up to 6 carbon atoms,
R$^{18}$ and R$^{19}$ are identical or different and denote phenyl, hydrogen or straight-chain or branched alkyl having up to 6 carbon atoms
or denote straight-chain or branched acyl having up to 8 carbon atoms, which is optionally substituted by a group of the formula —NR$^{20}$R$^{21}$,
in which
R$^{20}$ and R$^{21}$ are identical or different and denote hydrogen or straight-chain or branched acyl having up to 8 carbon atoms,
R$^6$ represents hydrogen, carboxyl or straight-chain or branched alkoxycarbonyl having up to 5 carbon atoms,
or represents straight-chain or branched alkyl having up to 6 carbon atoms, which is optionally substituted by hydroxyl or by a group of the formula —O—CO—R$^{22}$,
in which
R$^{22}$ denotes phenyl which is optionally substituted up to 3 times in an identical or different manner by halogen, hydroxyl or by straight-chain or branched alkyl having up to 5 carbon atoms,
or denotes straight-chain or branched alkyl or alkenyl each having up to 22 carbon atoms, each of which is optionally substituted by a group of the formula -OR$^{23}$,
in which
R$^{23}$ denotes hydrogen, benzyl, triphenylmethyl or straight-chain or branched acyl having up to 6 carbon atoms,
optionally in an isomeric form, and their salts.
2. Compounds of the formula according to claim 1, in which
R$^1$ and R$^2$, including the double bond connecting them, together form a phenyl ring or a cyclopentene, cyclohexene, cycloheptene, cyclooctene, oxocyclopentene, oxocyclohexene, oxocycloheptene or oxocyclooctene radical, which is optionally substituted up to 2 times in an identical or different manner by fluorine, chlorine, bromine, trifluoromethyl, carboxyl, hydroxyl, by straight-chain or branched alkoxy or alkoxycarbonyl each having up to 4 carbon atoms or by straight-chain or branched alkyl having up to 4 carbon atoms, which for its part can be substituted by hydroxyl or by straight-chain or branched alkoxy having up to 3 carbon atoms, $R^3$ and $R^4$, including the double bond, together form a radical of the formula

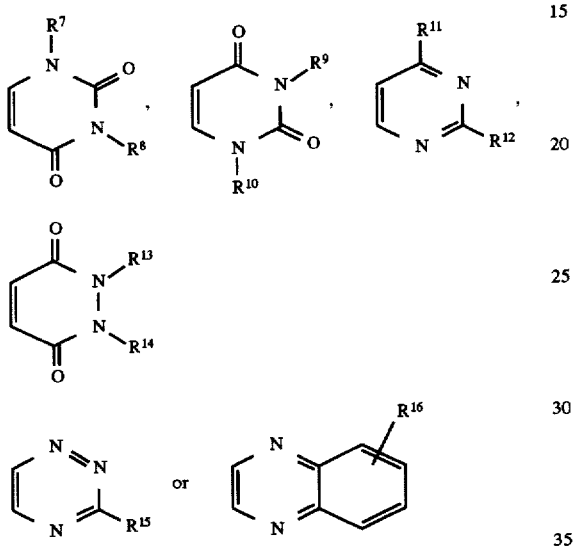

in which $R^7$, $R^8$, $R^9$, $R^{10}$, $R^{11}$, $R^{12}$, $R^{13}$, $R^{14}$, $R^{15}$ and $R^{16}$ are identical or different and denote hydrogen, straight-chain or branched alkoxy, alkylthio, acyl or alkoxycarbonyl each having up to 4 carbon atoms or straight-chain or branched alkyl having up to 4 carbon atoms, which is optionally substituted by hydroxyl, or $R^1$ and $R^2$, including the double bond, form a pyridyl ring, and $R^3$ and $R^4$, likewise including the double bond, together form a pyridyl ring, both pyridyl rings optionally being substituted up to 2 times in an identical or different manner by fluorine, chlorine, bromine, trifluoromethyl, carboxyl, hydroxyl, by straight-chain or branched alkoxy or alkoxycarbonyl each having up to 4 carbon atoms or by straight-chain or branched alkyl having up to 4 carbon atoms, which for its part is substituted by hydroxyl or by straight-chain or branched alkoxy having up to 3 carbon atoms, A and D are identical or different and represent hydrogen, fluorine, chlorine, bromine, trifluoromethyl, hydroxyl or straight-chain or branched alkyl or alkoxy each having up to 4 carbon atoms, E and L are identical or different and represent hydrogen, cyclopropyl, cyclobutyl, cyclopentyl, cyclohexyl, cycloheptyl, cyclooctyl or straight-chain or branched alkyl having up to 8 carbon atoms, which is optionally substituted by cyclopropyl, cyclopentyl or cyclohexyl, or represent phenyl which is optionally substituted by fluorine, chlorine or bromine, or E and L, together with the carbon atom, form a 4-7-membered cycloalkyl ring, $R^5$ represents phenyl, pyridyl, furyl, thienyl or imidazolyl, each of which is optionally substituted up to 2 times in an identical or different manner by nitro, carboxyl, fluorine, chlorine, bromine, cyano, by straight-chain or branched alkenyl or alkoxycarbonyl each having up to 4 carbon atoms or by straight-chain or branched alkyl having up to 5 carbon atoms, which is optionally substituted by hydroxyl, carboxyl or by straight-chain or branched alkoxy or alkoxycarbonyl each having up to 5 carbon atoms, and/or the cycles are optionally substituted by a group of the formula —$OR^{17}$ or —$NR^{18}R^{19}$, in which $R^{17}$ denotes hydrogen or straight-chain or branched alkyl or alkenyl each having up to 4 carbon atoms, $R^{18}$ and $R^{19}$ are identical or different and denote phenyl, hydrogen or straight-chain or branched alkyl having up to 5 carbon atoms, or denote straight-chain or branched acyl having up to 6 carbon atoms, which is optionally substituted by a group of the formula —$NR^{20}R^{21}$, in which $R^{20}$ and $R^{21}$ are identical or different and denote hydrogen or straight-chain or branched acyl having up to 6 carbon atoms, $R^6$ represents hydrogen, carboxyl or straight-chain or branched alkoxycarbonyl having up to 4 carbon atoms, or represents straight-chain or branched alkyl having up to 5 carbon atoms, which is optionally substituted by hydroxyl or by a group of the formula —O—CO—$R^{22}$, in which $R^{22}$ denotes phenyl which is optionally substituted up to 3 times in an identical or different manner by fluorine, chlorine, bromine, hydroxyl or by straight-chain or branched alkyl having up to 4 carbon atoms, or denotes straight-chain or branched alkyl or alkenyl each having up to 20 carbon atoms, each of which is optionally substituted by a group of the formula —$OR^{23}$, in which $R^{23}$ denotes hydrogen, benzyl, triphenylmethyl or straight-chain or branched acyl having up to 5 carbon atoms, optionally in an isomeric form, and their salts.

3. Compounds of the formula according to claim 1, in which $R^1$ and $R^2$, including the double bond connecting them, together form a phenyl ring or a cyclopentene, cyclohexene, cycloheptene, cyclooctene, oxocyclopentene, oxocyclohexene, oxocycloheptene or oxocyclooctene radical, which is optionally substituted up to 2 times in an identical or different manner by fluorine, chlorine, bromine, trifluoromethyl, carboxyl, hydroxyl, by straight-chain or branched alkoxy or alkoxycarbonyl each having up to 3 carbon atoms or by straight-chain or branched alkyl having up to 3 carbon atoms, which for its part can be substituted by hydroxyl, methoxy or ethoxy, $R^3$ and $R^4$, including the double bond, together form a radical of the formula

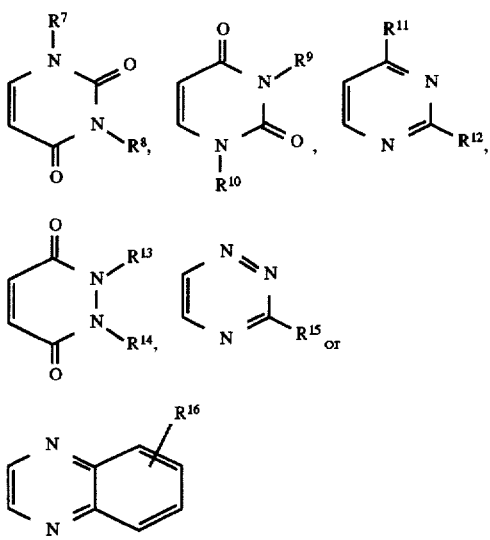

in which

R⁷, R⁸, R⁹, R¹⁰, R¹¹, R¹², R¹³, R¹⁴, R¹⁵ and R¹⁶ are identical or different and denote hydrogen, straight-chain or branched alkoxy or alkylthio each having up to 3 carbon atoms or straight-chain or branched alkyl having up to 3 carbon atoms, which is optionally substituted by hydroxyl, or R¹ and R², including the double bond, form a pyridyl ring, and R³ and R⁴, likewise including the double bond, together form a pyridyl ring, both pyridyl rings optionally being substituted up to 2 times in an identical or different manner by fluorine, chlorine, bromine, trifluoromethyl, carboxyl, hydroxyl, by straight-chain or branched alkoxy or alkoxycarbonyl each having up to 3 carbon atoms or by straight-chain or branched alkyl having up to 3 carbon atoms, which for its part is substituted by hydroxyl, methoxy or ethoxy, A and D are identical or different and
represent hydrogen, fluorine, chlorine, bromine or trifluoromethyl, E and L are identical or different and
represent hydrogen, cyclopropyl, cyclobutyl, cyclopentyl, cyclohexyl, cycloheptyl, cyclooctyl or straight-chain or branched alkyl having up to 6 carbon atoms, which is optionally substituted by cyclopentyl or cyclohexyl, or
represent phenyl which is optionally substituted by fluorine, chlorine or bromine, or E and L, together with the carbon atom, form a 5-7-membered cycloalkyl ring, R⁵ represents phenyl, pyridyl or thienyl, each of which is optionally substituted up to 2 times in an identical or different manner by nitro, carboxyl, fluorine, chlorine, bromine, cyano, by straight-chain or branched alkenyl or alkoxycarbonyl each having up to 3 carbon atoms or by straight-chain or branched alkyl having up to 4 carbon atoms, which is optionally substituted by hydroxyl, carboxyl or by straight-chain or branched alkoxy or alkoxycarbonyl each having up to 4 carbon atoms, and/or the cycles are optionally substituted by a group of the formula —OR¹⁷ or —NR¹⁸R¹⁹, in which R¹⁷ denotes hydrogen or straight-chain or branched alkyl or alkenyl each having up to 3 carbon atoms, R¹⁸ and R¹⁹ are identical or different and denote phenyl, hydrogen or straight-chain or branched alkyl having up to 4 carbon atoms, or denote straight-chain or branched acyl having up to 5 carbon atoms, which is optionally substituted by a group of the formula —NR²⁰R²¹, in which R¹⁹ and R²⁰ are identical or different and denote hydrogen or straight-chain or branched acyl having up to 5 carbon atoms, R⁶ represents hydrogen, carboxyl or straight-chain or branched alkoxycarbonyl having up to 3 carbon atoms, or represents straight-chain or branched alkyl having up to 4 carbon atoms, which is optionally substituted by hydroxyl or by a group of the formula —O—CO—R²², in which R²² denotes phenyl which is optionally substituted up to 3 times in an identical or different manner by straight-chain or branched alkyl having up to 3 carbon atoms, or denotes straight-chain or branched alkyl or alkenyl each having up to 19 carbon atoms, each of which is optionally substituted by a group of the formula —OR²³, in which R²³ denotes hydrogen, benzyl, triphenylmethyl or straight-chain or branched acyl having up to 4 carbon atoms, optionally in an isomeric form, and their salts.

4. Process for the preparation of compounds according to claim 1 characterized in that racemic or alternatively already enantiomerically pure carboxylic acids or their activated derivatives of the formula (II)

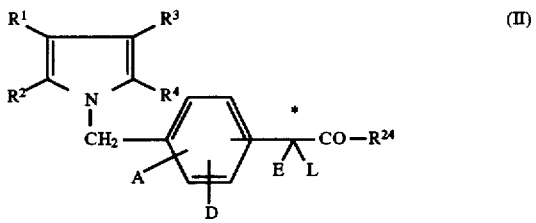

in which

R²⁴ represents hydroxyl or an activating radical, preferably chloride, are amidated with compounds of the formula (III)

in inert solvents, optionally in the presence of bases and/or auxiliaries.

5. A pharmaceutical composition comprising a compound according to claim 1 and a pharmaceutically acceptable carrier.

6. A method of treating atherosclerosis in a patient comprising administering to said patient an amount effective therefor of a compound according to claim 1.

7. A method of reducing or completely inhibiting the formation or release of ApoB-100-associated lipoproteins in a patient comprising administering to said patient an amount effective therefore of a compound according to claim 1.

* * * * *

UNITED STATES PATENT AND TRADEMARK OFFICE
CERTIFICATE OF CORRRECTION

PATENT NO. : 5,786,361
DATED : July 28, 1998
INVENTOR(S) : Muller, et al It is certified that error appears in the above-identified patent and that said Letters Patent is hereby corrected as shown below:

On the title page, under item [56], insert the following:

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 4 | 7 | 7 | 5 | 6 | 8 | 0 | Oct. 4, 1988 | Gillard, et al. | | | |
| | | 5 | 4 | 2 | 0 | 1 | 4 | 9 | May 30, 1995 | Muller, et al. | | | |
| | | 5 | 6 | 8 | 4 | 0 | 1 | 4 | Nov. 4, 1997 | Muller, et al. | | | |
| | | 5 | 5 | 2 | 1 | 2 | 0 | 6 | May 28, 1996 | Muller, et al. | | | |
| | | | | | | | | | | | | | |

FOREIGN PATENT OR PUBLISHED FOREIGN PATENT APPLICATION

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | | 2 | 3 | 4 | 7 | 0 | 8 | 9/2/87 | E.P. | | | | |
| | | | | | | | | | | | | | | |

Signed and Sealed this

Second Day of March, 1999

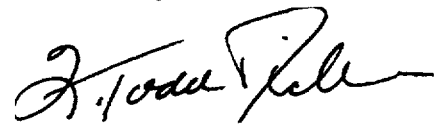

Attest:

Q. TODD DICKINSON

*Attesting Officer*    *Acting Commissioner of Patents and Trademarks*

UNITED STATES PATENT AND TRADEMARK OFFICE
CERTIFICATE OF CORRECTION

PATENT NO. : 5,786,361
DATED : July 28, 1998
INVENTOR(S) : Muller et al

It is certified that error appears in the above-indentified patent and that said Letters Patent is hereby corrected as shown below:

Title Page, [30], Foreign Application Priority Data     Delete "Apr. 11, 1997" and insert --Apr. 18, 1996--

Title Page, [56], References Cited     Delete "5,238,248" and insert --5,283,248--

Signed and Sealed this

Fifth Day of October, 1999

Attest:

Q. TODD DICKINSON

*Attesting Officer*     *Acting Commissioner of Patents and Trademarks*